United States Patent
Iwaki et al.

(10) Patent No.: US 7,410,613 B2
(45) Date of Patent: *Aug. 12, 2008

(54) HUMORAL TESTING APPARATUS

(75) Inventors: Yoshihide Iwaki, Asaka (JP); Kentarou Nakamura, Asaka (JP); Hideaki Tanaka, Asaka (JP); Yoshiki Sakaino, Asaka (JP); Kaoru Terashima, Asaka (JP); Hitoshi Shimizu, Asaka (JP)

(73) Assignee: Fujifilm Corporation, Tokyo (JP)

( * ) Notice: Subject to any disclaimer, the term of this patent is extended or adjusted under 35 U.S.C. 154(b) by 460 days.

This patent is subject to a terminal disclaimer.

(21) Appl. No.: 10/397,376

(22) Filed: Mar. 27, 2003

(65) Prior Publication Data

US 2003/0185711 A1  Oct. 2, 2003

(30) Foreign Application Priority Data

Mar. 28, 2002  (JP)  ............................. 2002-092229

(51) Int. Cl.
*G01N 21/78* (2006.01)
(52) U.S. Cl. ..................................... 422/82.05; 702/19
(58) Field of Classification Search .............. 422/82.05; 702/19
See application file for complete search history.

(56) References Cited

U.S. PATENT DOCUMENTS

| | | | |
|---|---|---|---|
| 4,526,753 A * | 7/1985 | Boger et al. ................... | 422/56 |
| 5,051,901 A | 9/1991 | Endo | |
| 5,112,490 A | 5/1992 | Turpen | |
| 5,408,535 A * | 4/1995 | Howard et al. .............. | 382/128 |
| 5,866,007 A | 2/1999 | Whitson et al. | |
| 5,919,356 A | 7/1999 | Hood | |
| 5,945,341 A * | 8/1999 | Howard, III ................. | 436/46 |
| 6,126,643 A | 10/2000 | Vaillancouert | |
| 6,192,168 B1 * | 2/2001 | Feldstein et al. ............. | 385/12 |
| 6,220,453 B1 | 4/2001 | Kitajima et al. | |
| 2001/0005488 A1 | 6/2001 | Hirao et al. | |
| 2001/0045387 A1 | 11/2001 | Amano et al. | |
| 2003/0113935 A1 * | 6/2003 | Carson et al. ............... | 436/165 |

FOREIGN PATENT DOCUMENTS

| | | |
|---|---|---|
| EP | 0 123 443 A2 | 10/1984 |
| EP | 0 272 407 A2 | 6/1988 |
| EP | 0 926 484 A2 | 6/1999 |
| EP | 1 018 648 A1 | 7/2000 |
| JP | 2000-74906 A | 3/2000 |
| JP | 2000-74910 A | 3/2000 |
| WO | WO-02/071063 A1 | 9/2002 |

* cited by examiner

*Primary Examiner*—Lyle A Alexander
(74) *Attorney, Agent, or Firm*—Birch, Stewart, Kolasch & Birch, LLP

(57) ABSTRACT

A humoral testing apparatus in which a measuring light is irradiated to a reagent area forming a color as a result of a reaction and an optical density of the reagent area is detected by a detecting operation of light intensity of the reflected light. The humoral testing apparatus enables a humoral test to be performed accurately in cases where nonuniformity occurs with the reaction of a reagent with a humoral sample within the reagent area, or in cases where fine dust is present within each detecting spot in the reagent areas. The light reflected from the reagent areas is detected with a two-dimensional photodetector. The independent light intensity detecting operations are performed with respect to the subareas of the reagent area of a reagent layer. A photo detection signal S, which represents the intensity of the reflected light is statistically processed with a signal processing section 51.

8 Claims, 12 Drawing Sheets

FIG.1
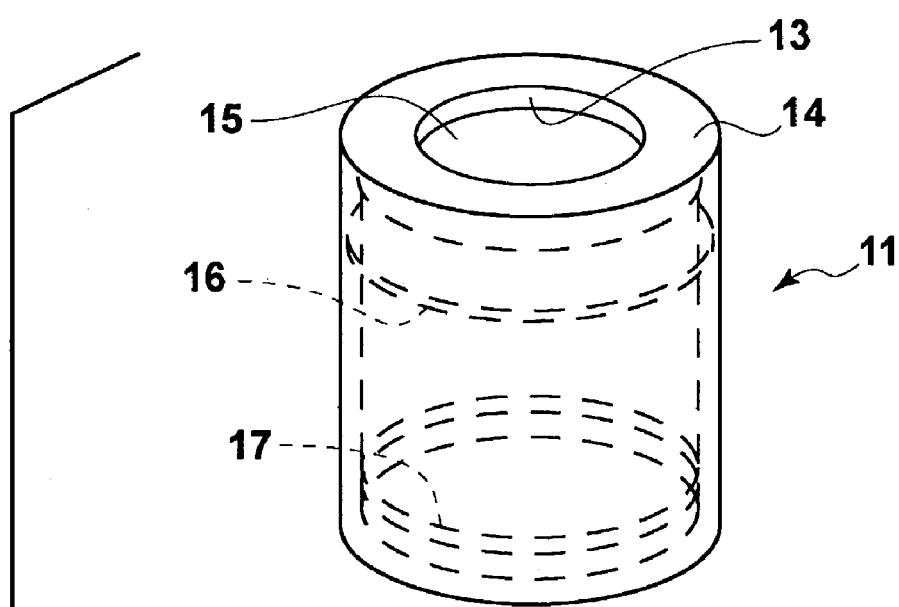
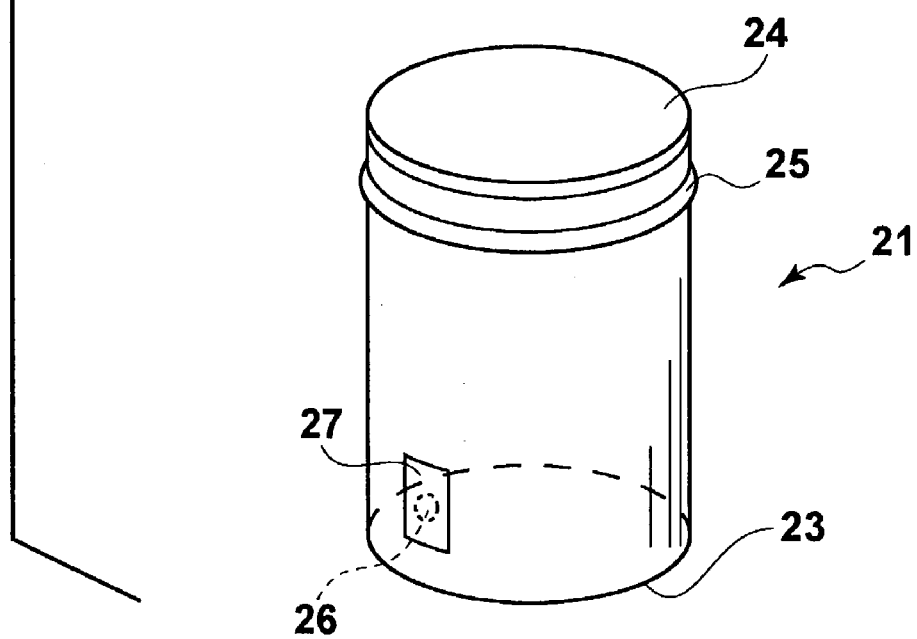

HUMORAL TESTING APPARATUS

BACKGROUND OF THE INVENTION

1. Field of the Invention

This invention relates to a humoral testing apparatus for use in performing tests on bodily fluids of humans and other animals.

2. Description of the Related Art

As blood testing units for use in performing tests of blood of humans and other animals, blood testing units having a slide-shaped support and a reagent layer carried on the slide-shaped support, which reagent layer is capable of undergoing a reaction with blood plasma or blood serum and forming a predetermined color, have heretofore been proposed. The blood testing units are proposed in, for example, U.S. Pat. No. 5,051,901.

In cases where the blood testing units described above are utilized, blood plasma or blood serum is spotted onto the reagent layer of the blood testing unit. Thereafter, light is irradiated to the reagent layer having formed a color, and an intensity of light reflected from the reagent layer is measured. In this manner, a concentration of a specific substance contained in the blood plasma or the blood serum, or the like, is capable of being quantitatively analyzed in accordance with the intensity of the reflected light. An example of an analysis apparatus for performing the blood tests in the manner described above is also disclosed in U.S. Pat. No. 5,051,901.

With regard to the blood testing unit described above, in which the reagent layer is formed on the slide-shaped support, in cases where nonuniformity occurs with the reaction of the reagent with the blood sample within each of the reagent areas, or in cases where fine dust, or the like, is present within each of the reagent areas, adverse effects on specific results of the light intensity detection due to the nonuniformity in reaction, the fine dust, or the like, may degrade the accuracy of the blood test.

Problems basically similar to the problems described above may occur in cases of the blood testing unit for performing tests on bodily fluids other than the blood of animals, such as urine, sweat, or cerebrospinal fluid.

SUMMARY OF THE INVENTION

The object of the present invention is to provide a humoral testing apparatus in which measuring light is irradiated to a reagent area forming a color as a result of a reaction and an intensity of the light reflected from the reagent area is detected, and thus an optical density of the reagent area is detected in accordance with the intensity of the reflected light, which humoral testing apparatus enabling a humoral test to be performed accurately in cases where nonuniformity occurs in the reaction of the reagent with a humoral sample within the reagent area, or in cases where fine dust, or the like, is present within the reagent area.

The present invention provides a humoral testing apparatus for use with a humoral testing unit, in which measuring light is irradiated to a reagent area of a reagent layer, the reagent area forming a color as a result of a reaction with a humoral sample, and an optical density of the reagent area is detected in accordance with a light intensity of the light reflected from the reagent area, comprising:

means for performing a plurality of independent light intensity detecting operation with respect to a plurality of subareas of the reagent area of the reagent layer, each of the independent light intensity detecting operations being performed for one of the plurality of the subareas of the reagent area; and means for processing statistically results of the plurality of the independent light intensity detecting operations performed with respect to the plurality of the subareas of the reagent area, a light intensity value representative of one of the reagent area being obtained from the statistical processing.

As the statistical processing described above, for example, processing for calculating a mean value, processing for calculating a median value, or processing for calculating a normal distribution of the detected light intensity values and calculating a mean value of the detected light intensity values, which fall within the range of ±2SD (where SD represents the standard deviation) around a detected light intensity value that is associated with the maximum frequency of occurrence, should preferably be employed.

With the humoral testing apparatus in accordance with the present invention, the plurality of the independent light intensity detecting operations are performed with respect to the subareas of the reagent area of the reagent layer, each of the independent light intensity detecting operations being performed for one of the plurality of the subareas of the reagent area. The results of the plurality of the independent light intensity detecting operations performed with respect to the plurality of the subareas of the reagent area are subjected to the statistical processing, the light intensity value representative of the reagent area being obtained from the statistical processing, and the thus obtained light intensity value representative of the reagent area is taken as the intensity of the light having been reflected from the reagent area. In cases where nonuniformity occurs with the reaction of the reagent with the blood plasma and/or the blood serum within the reagent area, or in cases where fine dust, or the like, is present within the reagent area, adverse effects of specific results of the light intensity detection due to the nonuniformity in reaction, the fine dust, or the like, are capable of being eliminated, and the blood test is capable of being performed accurately.

BRIEF DESCRIPTION OF THE DRAWINGS

FIG. 1 is an exploded perspective view showing a first embodiment of the blood testing unit in accordance with the present invention.

DESCRIPTION OF THE PREFFERED EMBODIMENTS

The present invention will hereinbelow be described with reference to the accompanying drawings.

Figure 2:
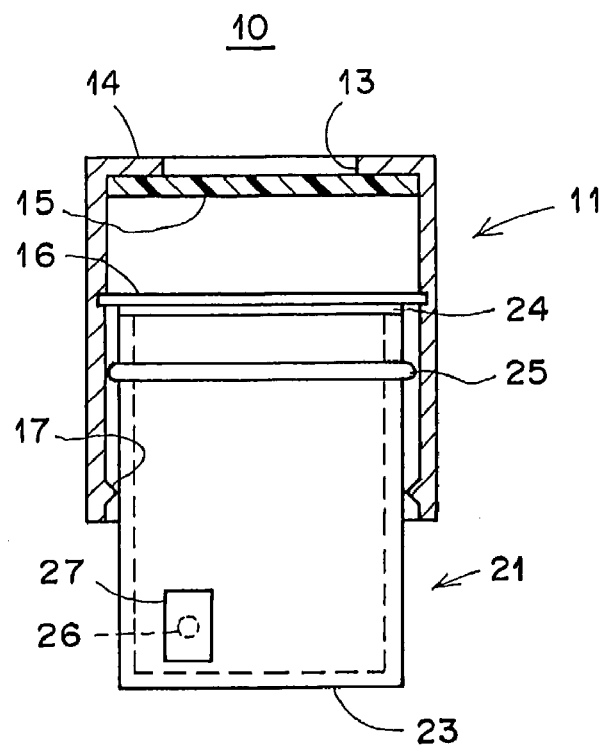
FIG. 2 is a partially cutaway side view showing the blood testing unit of FIG. 1.
Figure 5:
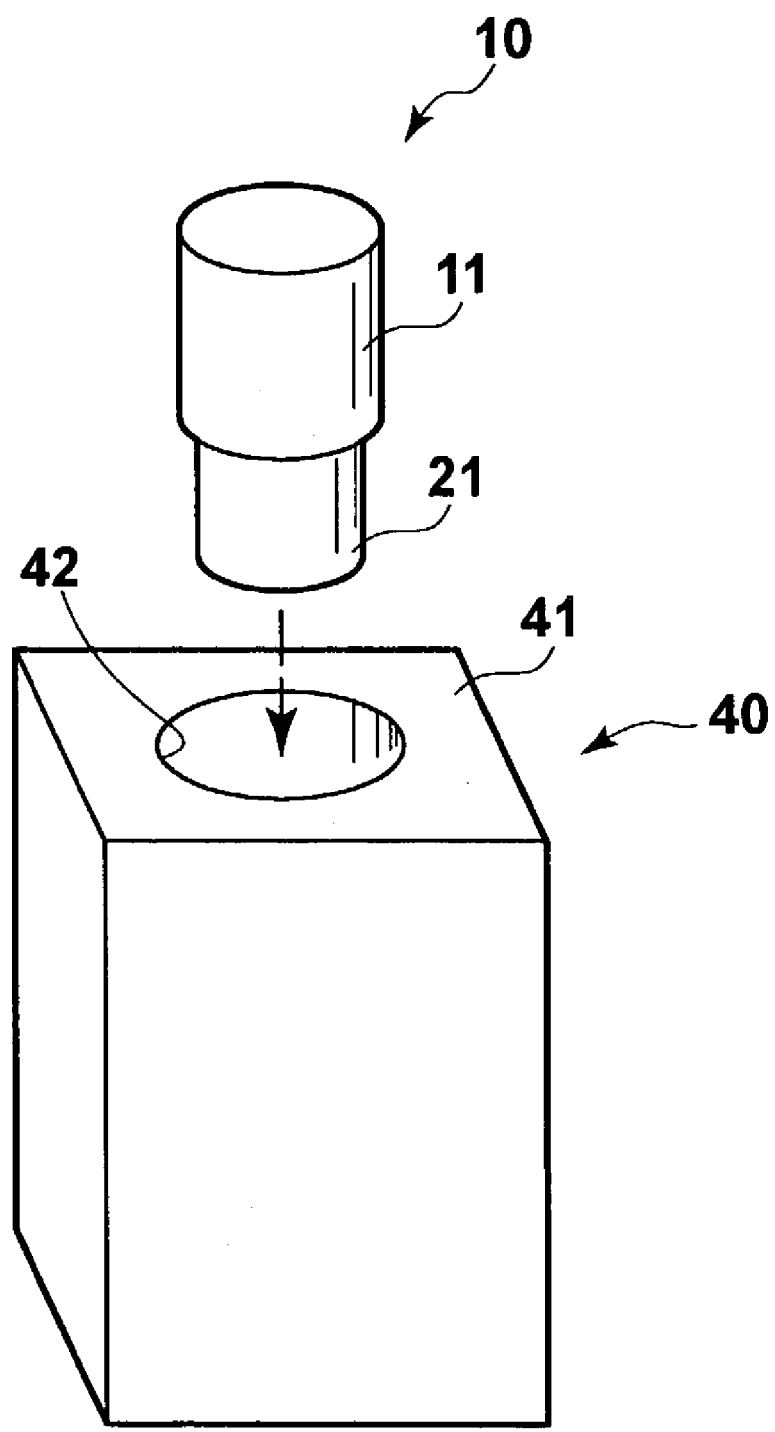
FIG. 5 is a perspective view showing a first embodiment of the blood testing apparatus in accordance with the present invention.
Figure 6:
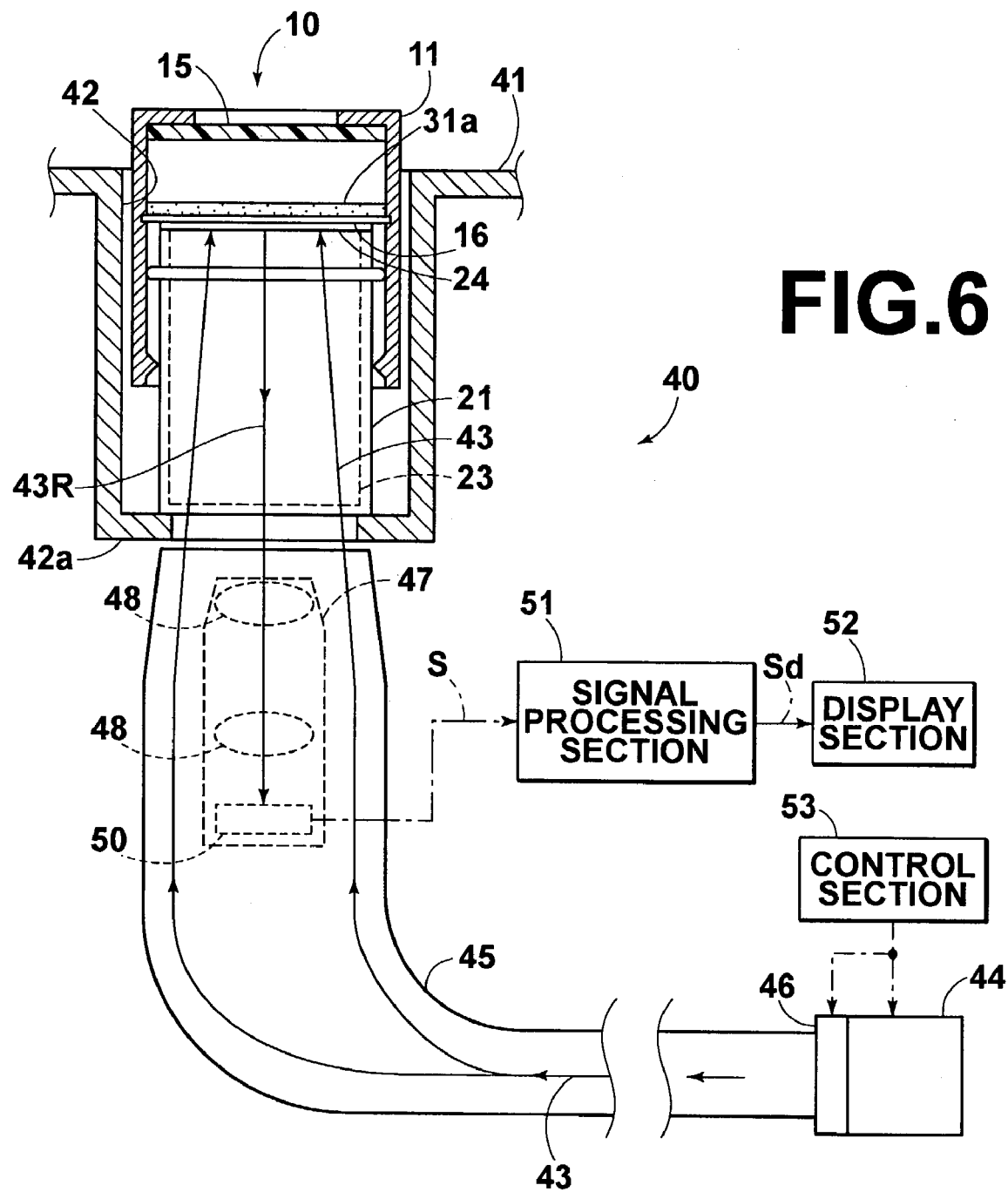
FIG. 6 is a partially cutaway side view showing the blood testing unit of FIG. 5.

FIG. 1 is an exploded perspective view showing a blood testing unit 10, which is used for a blood testing apparatus 40 (refer to FIG. 5 and FIG. 6). FIG. 2 is a partially cutaway side view of the blood testing unit 10. Firstly, the blood testing unit 10 will hereinbelow be described.

As illustrated in FIG. 1 and FIG. 2, the blood testing unit 10 comprises a circular cylinder-shaped outer vessel body 11, whose lower end portion in FIG. 1 and FIG. 2 is open, and a circular cylinder-shaped inner vessel body 21, which has a bottom wall 23 at lower end portion in FIG. 1 and FIG. 2. By way of example, each of the outer vessel body 11 and the inner vessel body 21 is made from a transparent synthetic resin. The outer vessel body 11 has a size of, for example, an outer diameter of 15 mm× a height of 30 mm. The inner vessel body 21 has a size of, for example, an outer diameter of 10 mm× a height 30 mm. Alternatively, each of the outer vessel body 11 and the inner vessel body 21 may be made from glass, or the like.

The outer vessel body 11 has an upper wall 14 at an end portion on the upper side in FIG. 1 and FIG. 2. The upper wall 14 is provided with a circular opening 13. Ordinarily, the opening 13 is closed by a rubber film 15, which is adhered to an inner surface of the upper wall 14. As will be described later, the rubber film 15 constitutes the blood introducing section. Also, a circular blood constituent separating membrane 16 is formed with an insert molding process and held within the outer vessel body 11. The blood constituent separating membrane 16 is constituted of a porous structure material. The porous structure material acts such that, when a blood sample is supplied to the porous structure material, the porous structure material allows the blood plasma and/or blood serum to pass therethrough and obstructs solid constituents from passing therethrough. In this embodiment, by way of example, a polysulfone membrane having a pore diameter falling within the range of 0.5 μm to 50 μm is utilized as the porous structure material. Further, an annular engagement section 17 is formed on an inner peripheral wall of the outer vessel body 11. The annular engagement section 17 projects inwardly from the inner peripheral wall of the outer vessel body 11 and at a position close to an open end of the outer vessel body 11, which open end is formed at the lower end of the outer vessel body 11 in FIG. 1 and FIG. 2.

The lower end of the inner vessel body 21 in FIG. 1 and FIG. 2 is closed by the bottom wall 23. An upper end of the inner vessel body 21 is open, and a reagent layer 24 is fitted to the upper end of the inner vessel body 21. Also, an O-ring 25 is fitted onto an outer peripheral wall of the inner vessel body 21 and at a position comparatively close to the upper end of the inner vessel body 21. Further, an air introducing aperture 26, which communicates the interior of the inner vessel body 21 and the exterior of the inner vessel body 21 to each other, is formed through the peripheral wall of the inner vessel body 21. The air introducing aperture 26 is closed by a sheet-shaped sealing member 27, which is adhered to the outer peripheral wall surface of the inner vessel body 21.

By way of example, the reagent layer 24 comprises a nitrocellulose porous membrane having a pore diameter of 0.45 μm (supplied by Millipore Corporation), two glucose detecting spots, which are of the pigment types and have absorption characteristics such that the maximum absorption wavelength is in the vicinity of 505 nm, and two uric acid detecting spots, which are of the pigment types and have absorption characteristics such that the maximum absorption wavelength is in the vicinity of 650 nm, the four detecting spots being formed on the nitrocellulose porous membrane. The reagent layer 24 may be prepared in the manner described below. Specifically, for example, an MES buffer solution, which contains glucose oxidase, peroxidase, 1,7-dihydroxy naphthalene, and 4-amino antipyrine and has been adjusted to a pH value falling within the range of 5.5 to 6.5, is spotted to two positions on the nitrocellulose porous membrane. Also, a buffer solution, which contains uricase, peroxidase, and a diallyl imidazole type of leuco-pigment, is spotted to two positions on the nitrocellulose porous membrane. The thus formed four spots are then dried, and the reagent layer 24 is thus obtained. Since the support of the reagent layer 24 is formed from the nitrocellulose porous membrane described above, when the blood plasma and/or the blood serum is supplied to the reagent layer 24, the blood plasma and/or blood serum spreads in the spread direction of the reagent layer 24.

Figure 3:
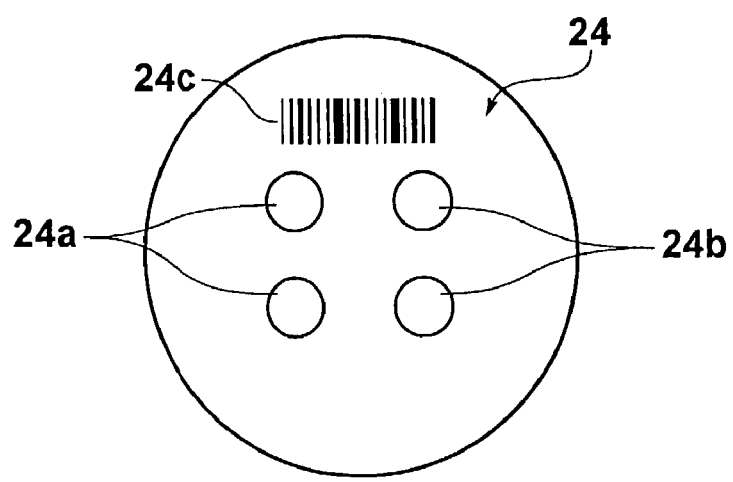
FIG. 3 is a plan view showing a reagent layer of the blood testing unit of FIG. 1.

FIG. 3 is a plane view showing the reagent layer 24 described above. In FIG. 3, reference numerals 24a, 24a denote the two glucose detecting spots, and reference numerals 24b, 24b denote the two uric acid detecting spots. In this embodiment, the reagent layer 24 is also provided with a bar code 24c acting as a mark, which represents information concerning the blood testing unit 10, i.e. a production serial number of the blood testing unit 10, a kind of the blood testing unit 10, or the like. The bar code 24c will be described in detail later.

As illustrated in FIG. 2, the outer vessel body 11 and the inner vessel body 21 are combined with each other in order to constitute the blood testing unit 10. When the inner vessel body 21 is accommodated within the outer vessel body 11, the O-ring 25 of the inner vessel body 21 and the annular engagement section 17 of the outer vessel body 11 interfere slightly with each other. However, in cases where the inner vessel body 21 is pushed slightly forcibly into the outer vessel body 11, the peripheral wall of the outer vessel body 11 and the O-ring 25 of the inner vessel body 21 undergo elastic deformation, and the O-ring 25 is thus capable of passing over the annular engagement section 17.

In the state shown in FIG. 2, the inner vessel body 21 is capable of moving in the major axis direction, i.e. vertically in FIG. 2, within the outer vessel body 11. At this time, the inner vessel body 21 slides on the inner peripheral wall of the outer vessel body 11 with the O-ring 25 intervening therebetween. Therefore, an enclosed space defined by the inner vessel body 21 and the outer vessel body 11 is formed. Specifically, in this embodiment, the outer vessel body 11 and the inner vessel body 21 co-operate to constitute a closed vessel, such that the interior of the closed vessel is kept in a water-tight state with respect to the exterior.

Also, particularly, the enclosed space described above is kept in an approximately hermetically sealed state with respect to the exterior by the O-ring 25. Therefore, when the inner vessel body 21 is pulled downwardly, i.e. in the direction heading away from the upper wall 14 of the outer vessel body 11, from the state shown in FIG. 2, the pressure within the enclosed space is reduced to a negative pressure. When the inner vessel body 21 is thus pulled and moved downwardly by a predetermined distance, the O-ring 25 of the inner vessel body 21 and the annular engagement section 17 of the outer vessel body 11 come into engagement with each other. Therefore, the inner vessel body 21 is prevented from separating from the outer vessel body 11.

Figure 4:
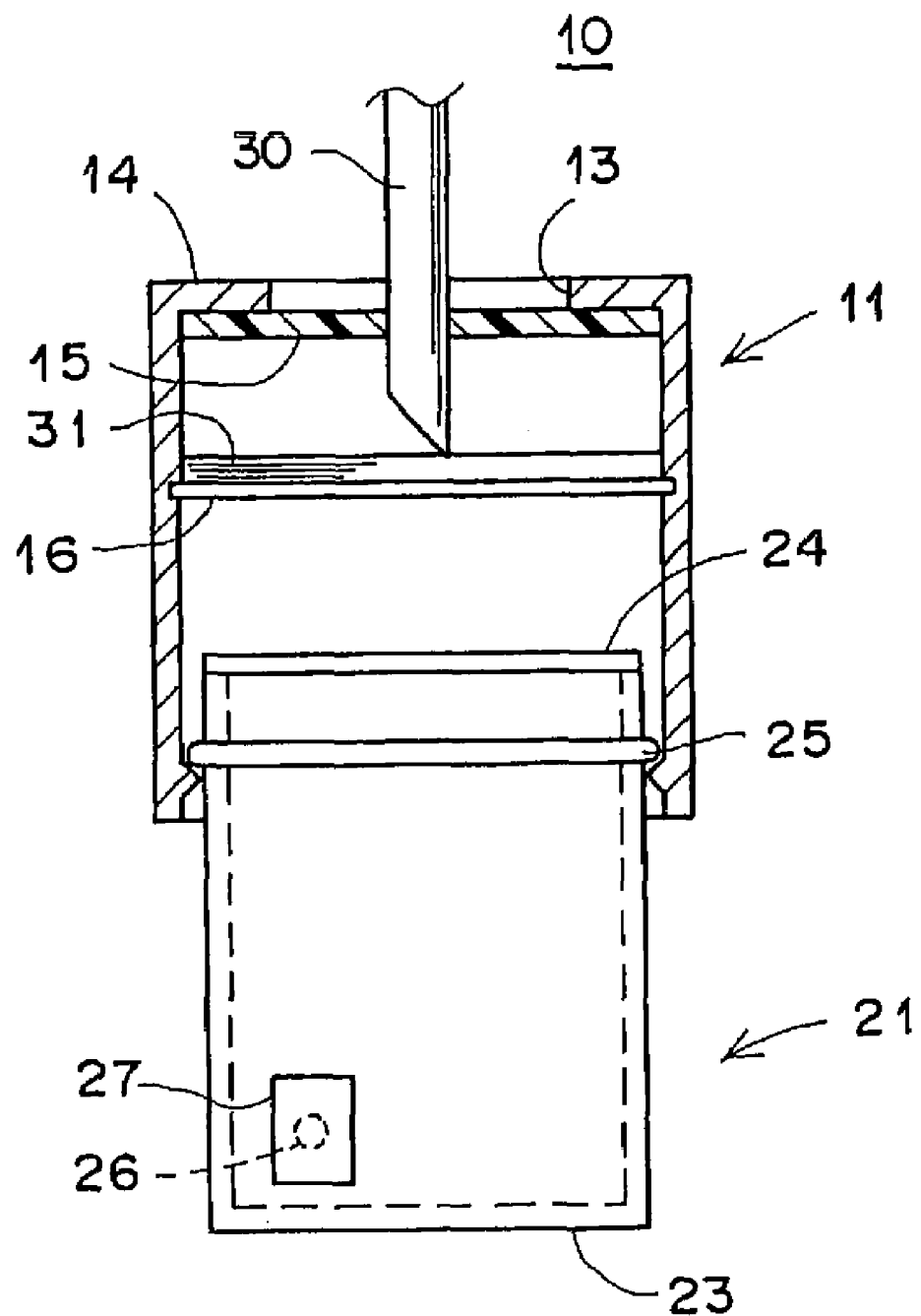
FIG. 4 is a partially cutaway side view showing the blood testing unit of FIG. 1 in a state in which a blood sample is introduced into the blood testing unit.

How a blood test is performed by use of the blood testing unit 10 described above will be described hereinbelow. Firstly, how an operation for taking a blood sample is performed will be described hereinbelow. In order for the blood sample to be taken, the inner vessel body 21 is pulled in the direction heading away from the upper wall 14 of the outer vessel body 11 in the manner described above, and the pressure within the enclosed space, which is defined by the inner vessel body 21 and the outer vessel body 11, is thus set at a negative pressure. The thus set state is illustrated in FIG. 4. Thereafter, as illustrated in FIG. 4, one tip of a blood sampling needle 30, whose other tip has been stuck in, for example, the upper arm of a human body, is stuck through the rubber film 15 of the outer vessel body 11 into the enclosed space described above. As a result, since the pressure within the enclosed space has been set at the negative pressure, whole blood 31 passes through the blood sampling needle 30 and is thus introduced into the enclosed space. As illustrated in FIG. 4, the whole blood 31 spreads over the blood constituent separating membrane 16. Solid constituents of the whole blood 31 are caught on the surface of the blood constituent separating membrane 16, and the blood plasma and/or the blood serum passes through the blood constituent separating membrane 16.

There is a correlation between the number of the amount of the whole blood 31, which is taken into the blood testing unit 10 in the manner described above, and the distance by which the inner vessel body 21 is pulled downwardly from the state shown in FIG. 2. The correlation has been confirmed with blood sampling experiments, which were conducted under conditions having been set to be uniform with the cases where the whole blood 31 is taken by use of the blood testing unit 10 in the manner described above. Specifically, for example, in cases where the distance by which the inner vessel body 21 is pulled downwardly is set at 1 cm, 2 cm, and 4 cm, the amount of the whole blood 31 taken into the blood testing unit 10 is capable of being set at 10 µl (microliter), 20 µl, and 40 µl, respectively.

In this embodiment, as described above, the pressure within the enclosed space defined by the inner vessel body 21 and the outer vessel body 11 is set at the negative pressure, and thereafter the blood sampling needle 30 is stuck through the rubber film 15. Alternatively, after the blood sampling needle 30 has been stuck through the rubber film 15, the inner vessel body 21 may be pulled downwardly, and the pressure within the enclosed space may thus be set at the negative pressure.

After the whole blood 31 has been supplied into the blood testing unit 10 in the manner described above, the blood sampling needle 30 is pulled out from the rubber film 15. At this time, the hole made by the blood sampling needle 30 remains in the rubber film 15. However, since the rubber film 15 has a high elasticity, in so far as the hole is left as it is, the hole is kept in the closed state by the high elasticity of the rubber film 15, and therefore problems do not occur such as the whole blood 31 leaking through the hole to the exterior of the blood testing unit 10. Also, when the blood sampling needle 30 is being stuck through the rubber film 15, the boundary between the outer peripheral wall of the blood sampling needle 30 and the rubber film 15 is kept in an approximately sealed state by the high elasticity of the rubber film 15. Therefore, the region within the blood testing unit 10 is kept in the negative pressure state until the whole blood 31 has been introduced into the blood testing unit 10. When the whole blood 31 has been introduced into the blood testing unit 10, the pressure within the blood testing unit 10 returns to the atmospheric pressure.

How a photometric operation is performed will be described hereinbelow. FIG. 5 is a perspective view showing a blood testing apparatus 40, which is a first embodiment of the blood testing apparatus in accordance with the present invention. FIG. 6 is a partially cutaway side view showing the blood testing unit 40 of FIG. 5. As illustrated in FIG. 5 and FIG. 6, the blood testing apparatus 40 comprises a unit receiving section 42 constituted of a circular cylinder-shaped hole for receiving the blood testing unit 10, which hole is open at a casing top surface 41. The blood testing unit 10 is accommodated in the unit receiving section 42 with the inner vessel body 21 facing down. Thereafter, the outer vessel body 11 is slightly pushed down and moved with respect to the inner vessel body 21. As a result, the blood constituent separating membrane 16 of the outer vessel body 11 comes into contact with the reagent layer 24 of the inner vessel body 21. This state is illustrated in FIG. 6. Since the reagent layer 24 has been formed in parallel with the blood constituent separating membrane 16, the entire area of the reagent layer 24 and the entire area of the blood constituent separating membrane 16 come into contact with each other.

As described above, solid constituents 31a of the whole blood 31 are caught on the upper side of the blood constituent separating membrane 16, and the blood plasma and/or the blood serum passes through the blood constituent separating membrane 16. Therefore, when the reagent layer 24 of the inner vessel body 21 comes into contact with the blood constituent separating membrane 16 in the manner described above, the blood plasma and/or the blood serum spreads over the reagent layer 24. Each of the buffer solutions (i.e., the reagents) of the glucose detecting spots 24a, 24a and the uric acid detecting spots 24b, 24b, which have been formed on the reagent layer 24, undergoes a reaction with the blood plasma and/or the blood serum and forms a color as a result of the reaction.

As illustrated in detail in FIG. 6, the blood testing apparatus 40 comprises a light source unit 44 for producing measuring light 43. The blood testing apparatus 40 also comprises a light guide member 45 for guiding the measuring light 43 having been produced by the light source unit 44. The light guide member 45 may be constituted of, for example, an optical fiber. The blood testing apparatus 40 further comprises a filter unit 46, which is located at an intermediate point of the light guide member 45 and selects the wavelength of the measuring light 43. The blood testing apparatus 40 still further comprises a light intensity measuring section 47, which is located within the light guide member 45 at a position in the vicinity of a light radiating end portion of the light guide member 45.

The light source unit 44 comprises a light emitting diode, which produces light having wavelengths in the vicinity of 505 nm, and a light emitting diode, which produces light having wavelengths in the vicinity of 650 nm. Either one of the two light emitting diodes is actuated selectively. The filter unit 46 comprises a filter, which transmits only light having a wavelength of 505 nm, and a filter, which transmits only light having a wavelength of 650 nm. Either one of the two filters is selectively inserted into an optical path within the light guide member 45. In lieu of the two light emitting diodes described above being utilized, a white light emitting diode for producing white light, which contains light having wavelengths in the vicinity of 505 nm and light having wavelengths in the vicinity of 650 nm, may be utilized.

The filter selecting operation of the filter unit 46 and the light emitting diode selecting and actuating operation are controlled by a common control section 53 in a manner interlocked with each other. Specifically, in cases where the light emitting diode for producing the light having the wavelengths in the vicinity of 505 nm is actuated, the filter, which transmits only the light having the wavelength of 505 nm, is inserted into the optical path. Also, in cases where the light emitting diode for producing the light having the wavelengths in the vicinity of 650 nm is actuated, the filter, which transmits only the light having the wavelength of 650 nm, is inserted into the optical path.

The light guide member 45 is located such that the light radiating end portion of the light guide member 45 faces the inner vessel body 21 of the blood testing unit 10, which has been accommodated in the unit receiving section 42 of the blood testing apparatus 40.

The light intensity measuring section 47 comprises an objective lens 48 for operating such that, when the measuring light 43 is irradiated to the reagent layer 24 of the inner vessel body 21 and is reflected as reflected light 43R from the reagent layer 24, the objective lens 48 collects the reflected light 43R. The light intensity measuring section 47 also comprises an image forming lens 49 for forming an image of the reflected light 43R, which has been collected by the objective lens 48. The light intensity measuring section 47 further comprises a two-dimensional photodetector 50 located at the position at which the image of the reflected light 43R is formed. The two-dimensional photodetector 50 may be constituted of a CCD image sensor, or the like.

How the blood testing apparatus 40 having the constitution described above operates will be described hereinbelow. When the blood testing unit 10 has been accommodated in the unit receiving section 42, the light source unit 44 and the filter unit 46 are controlled by the control section 53 in the manner described above, and the measuring light 43 having the wavelength of 505 nm and the measuring light 43 having the wavelength of 650 nm are irradiated alternately at intervals of, for example, 0.1 second through the light guide member 45 to the reagent layer 24 of the inner vessel body 21. In FIG. 6, of the measuring light 43 radiated out in a divergent light state from the light radiating end portion of the light guide member 45, only the light components traveling toward the areas of the reagent layer 24, at which areas the glucose detecting spots 24a, 24a and the uric acid detecting spots 24b, 24b have been formed, are illustrated. The intensity of the reflected light 43R having been reflected from the reagent layer 24 is detected by the two-dimensional photodetector 50.

Each of the buffer solution (i.e., the reagent) of the glucose detecting spots 24a, 24a and the uric acid detecting spots 24b, 24b, which have been formed on the reagent layer 24, has formed the color as a result of the reaction with the blood plasma and/or the blood serum to be tested. The optical density of each of the glucose detecting spots 24a, 24a and the uric acid detecting spots 24b, 24b is measured at intervals of 0.1 second. Specifically, the two-dimensional photodetector 50 has been divided into pixels and is capable of detecting the intensity of the reflected light 43R with respect to each fine point on the reagent layer 24. Therefore, the optical density of each of the glucose detecting spots 24a, 24a and the uric acid detecting spots 24b, 24b, whose optical density changes with the passage of time, is capable of being measured in accordance with a photo detection signal S obtained from the two-dimensional photodetector 50.

In order for the optical density of each of the glucose detecting spots 24a, 24a and the uric acid detecting spots 24b, 24b to be measured in accordance with the photo detection signal S obtained from the two-dimensional photodetector 50, it is necessary that a correspondence relationship between the positions on a photo detecting surface of the two-dimensional photodetector 50 and the positions on the reagent layer 24 is specified. For such purposes, the inner vessel body 21 maybe accommodated always in a predetermined orientation in the unit receiving section 42. Specifically, for example, a position matching mark may be attached to one position on the outer peripheral wall of the inner vessel body 21, and a position matching mark may be attached to one position on the inner peripheral wall of the unit receiving section 42. Then, the blood testing unit 10 may be accommodated in the unit receiving section 42 such that the positions of the two position matching marks coincide with each other.

The photo detection signal S, which represents the intensity of the reflected light 43R with respect to each of the glucose detecting spots 24a, 24a and the uric acid detecting spots 24b, 24b, is fed into a signal processing section 51. In accordance with the intensity of the reflected light 43R, the signal processing section 51 calculates the optical density of each of the glucose detecting spots 24a, 24a and the uric acid detecting spots 24b, 24b. Also, the signal processing section 51 previously stores information representing calibration curves, which have been formed in accordance with results of experiments and represent relationship between concentration of glucose and uric acid and the optical densities of the glucose detecting spots 24a, 24a and the uric acid detecting spots 24b, 24b. In accordance with the calibration curves, the signal processing section 51 calculates the concentrations of glucose and uric acid from the optical densities of the detecting spots, whose optical densities change with the passage of time. Further, the signal processing section 51 feeds a signal Sd, which represents the concentrations of glucose and uric acid having thus been calculated, into a displaying section 52. In the displaying section 52, the concentrations of glucose and uric acid represented by the signal Sd are displayed as the test results. The conversion of the intensity of the reflected light 43R into the optical density is made by utilizing optical calculation techniques, such as a Lambert-Beer's law and a diffuse reflection formula.

Certain kinds of reagents constituting the detecting spots of the reagent layer 24 require supply of oxygen, such that the reagents are capable of undergoing reactions with substances to be detected, or such that the reagents are capable of completing the reactions with substances to be detected within a predetermined reaction time. In cases where such kinds of reagents are utilized, after the whole blood 31 has been introduced into the blood testing unit 10 in the manner described above, the sealing member 27 having been adhered to the outer peripheral wall surface of the inner vessel body 21 is removed from the outer peripheral wall surface of the inner vessel body 21. As a result, the air introducing aperture 26 having been closed by the sealing member 27 is opened, and oxygen contained in air is supplied through the air introducing aperture 26 to the region within the inner vessel body 21, i.e. to the reagent layer 24. In cases where the air introducing aperture 26 is again closed by the sealing member 27 after air has been introduced into the inner vessel body 21, problems, such as the person in charge of the blood test coming in contact with the blood constituents within the blood testing unit 10, are capable of being prevented.

In lieu of the sheet-shaped sealing member 27 described above being utilized, a plug-shaped sealing member for closing the air introducing aperture 26 may be utilized. In such cases, after air has been introduced into the inner vessel body 21, the air introducing aperture 26 may again be closed by the plug-shaped sealing member. In this manner, problems, such as the person in charge of the blood test coming into contact with the blood constituents within the blood testing unit 10, are capable of being prevented.

Ordinarily, in cases where the blood test is performed, the blood testing unit 10 is kept at a predetermined temperature by use of an incubator (not shown), and the blood plasma and/or blood serum is caused to react with the reagent at a predetermined temperature higher than room temperature, e.g. at a temperature of 37° C. In such cases, a substance capable of generating heat in the presence of water should preferably be added to the aforesaid nitrocellulose porous membrane, which constitutes the reagent layer 24 and allows the blood plasma and/or the blood serum to spread. In such cases, when the blood plasma and/or the blood serum containing water spreads through the reagent layer 24, the reagent layer 24 is heated with heat generated by the aforesaid substance. In cases where the reagent layer is capable of being heated preliminarily with heat generated by the aforesaid substance in the manner described above, the time required for the blood testing unit 10 to reach the predetermined temperature in the incubator is capable of being kept short, and therefore the blood test is capable of being performed with a high efficiency.

As the substance capable of generating heat in the presence of water, an alumino-silicate, such as zeolite, slacked lime, a mixture of iron powder and an oxidizing agent, or the like, may be employed.

In the first embodiment of the blood testing apparatus in accordance with the present invention, the light guide member 45 is located such that the light radiating end portion of the light guide member 45 is in contact with a lower surface 42a of a bottom plate of the unit receiving section 42. Therefore, the distance between the objective lens 48 of the light intensity measuring section 47 and the reagent layer 24, the distance between the image forming lens 49 of the light intensity measuring section 47 and the reagent layer 24, and the distance between the two-dimensional photodetector 50 of the light intensity measuring section 47 and the reagent layer 24 are kept at predetermined values.

In the first embodiment of the blood testing apparatus in accordance with the present invention, the concentrations of the specific constituents of the blood plasma and/or the blood serum are calculated in accordance with the calibration curves in the manner described. Alternatively, instead of the concentrations of the specific constituents of the blood plasma and/or the blood serum being calculated, the signal processing section 51 may perform only the processing for calculating the optical density of each of the glucose detecting spots 24a, 24a and the uric acid detecting spots 24b, 24b of the reagent layer 24, and the calculated optical densities may be displayed in the displaying section 52. As another alternative, the signal processing section 51 may output a signal, which represents the calculated optical densities, to the exterior.

As described above, the blood testing unit 10, which is the first embodiment of the blood testing unit in accordance with the present invention, comprises the closed vessel, which is constituted of the outer vessel body 11 and the inner vessel body 21, the blood constituent separating membrane 16, and the reagent layer 24, which are located within the closed vessel. Therefore, with the blood testing unit 10, the blood test is capable of being performed by introducing the whole blood 31 into the closed vessel, irradiating the measuring light 43 from the exterior of the closed vessel to the reagent layer 24, which has formed the color as a result of the reaction, and measuring the intensity of the reflected light 43R having been reflected from the reagent layer 24, the measurement being made from the exterior of the closed vessel. Specifically, the blood test is capable of being performed such that, after the blood sample has been introduced into the closed vessel, the person in charge of the blood test may not come in contact with the blood constituents, which are present within the closed vessel. Accordingly, with the blood testing unit 10, problems, such as the person in charge of the blood test coming in contact with the blood sample and catching an infectious disease, are capable of being prevented.

As described above, the blood testing unit 10 is constituted such that there is substantially no risk of persons coming in contact with the blood sample from the exterior of the blood testing unit 10. Therefore, after the blood testing unit 10 has been used for the blood test, the blood testing unit 10 may be processed with, for example, an autoclave, and may then be disposed. Accordingly, the blood testing unit 10 is capable of being utilized as a disposable blood testing unit.

Whether the blood testing unit 10 has already been used or has not yet been used for the blood test is capable of being confirmed by investigating whether each of the glucose detecting spots 24a, 24a and the uric acid detecting spots 24b, 24b of the reagent layer 24 has formed or has not formed the predetermined color, or whether a mark due to the blood sampling needle 30 is or is not left on the rubber film 15. Alternatively, such that it is capable of being confirmed more accurately whether the blood testing unit 10 has already been used or has not yet been used for the blood test, the reagent capable of undergoing the reaction with the blood sample and forming the color as a result of the reaction may be utilized such that letters, such as "used," may appear on the reagent layer 24 as a result of the reaction.

Also, with the blood testing unit 10, the blood plasma and/or the blood serum is separated from the whole blood 31 by the blood constituent separating membrane 16, which is located within the closed vessel. Therefore, with the blood testing unit 10, particular operations for setting the blood testing unit 10 on a centrifugal separator in order to separate the blood plasma and/or the blood serum from the whole blood 31, which require considerable time and labor, need not be performed, and the blood test is capable of being performed with a simple operation.

Particularly, with the blood testing unit 10, as described above, at least either one of the outer vessel body 11 and the inner vessel body 21 may be moved with respect to the other in the direction heading away from each other, and the pressure in the enclosed space is thus capable of being set at the negative pressure. In cases where the pressure in the enclosed space within the blood testing unit 10 is thus set at negative pressure, and the blood sampling needle 30 is then stuck through the rubber film 15, the whole blood 31 is capable of being sucked strongly into the enclosed space of the closed vessel. Alternatively, the blood sampling needle 30 may be stuck through the rubber film 15, and the pressure in the enclosed space may then be set at the negative pressure. Also, in this case, the blood sample is capable of being sucked strongly into the enclosed space of the closed vessel. As a result, a predetermined amount of the whole blood 31 is capable of being sampled quickly into the closed vessel, and the efficiency with which the blood test is performed is capable of being enhanced.

Further, with the blood testing unit 10, the blood constituent separating membrane 16 is constituted of the porous structure material, which allows the blood plasma and/or the blood serum to pass therethrough and obstructs the solid constituents from passing therethrough. Therefore, the structure for the separation of the blood plasma and/or the blood serum from the whole blood 31 is capable of being kept simple. Accordingly, the blood testing unit 10 is advantageous for keeping the size of the blood testing unit small. Furthermore, particularly, the polysulfone membrane, which has the pore diameter falling within the range described above, is utilized as the porous structure material. In such cases, the effects of separating the blood plasma and/or the blood serum from the whole blood 31 are capable of being obtained more reliably, and the reliability of the blood test is capable of being enhanced.

Also, with the blood testing unit 10, the blood constituent separating membrane 16 is formed with the insert molding process and is thus combined with the outer vessel body 11 into an integral body. Therefore, the blood constituent separating membrane 16 is secured tightly to the inner peripheral surface of the outer vessel body 11 without any gap being formed between the blood constituent separating membrane 16 and the inner peripheral surface of the outer vessel body 11 over the entire perimeter of the blood constituent separating membrane 16. In such cases, problems, such as the whole blood 31, from which the blood plasma and/or the blood serum has not yet been separated, leaking through a gap between the blood constituent separating membrane 16 and the inner peripheral surface of the outer vessel body 11 toward the reagent layer 24, are capable of being prevented. Accordingly, problems, such as the whole blood 31 adhering to the reagent layer 24 and obstructing the blood test, or an inaccurate blood test being made due to the whole blood 31 adhering to the reagent layer 24, are capable of being prevented.

Further, with the blood testing unit 10, the rubber film 15 constituting the blood introducing section is formed at the upper wall 14 of the outer vessel body 11. In such cases, for example, the blood testing unit 10 may be held in a state in which the rubber film 15 is located on the side remote from the person in charge of the blood test, and the inner vessel body 21 may be pulled toward the person in charge of the blood test. With the holding and pulling operation described above, the pressure in the enclosed space of the blood testing unit 10 is capable of being set at the negative pressure. The holding and pulling operation described above is markedly easy to perform, and therefore the introduction of the blood sample into the blood testing unit 10 is capable of being performed easily and reliably with the holding and pulling operation described above.

Furthermore, with the blood testing unit 10, the bottom wall 23 of the inner vessel body 21 is formed at the end portion of the inner vessel body 21, which end portion is remote from the upper wall 14 of the outer vessel body 11. Therefore, the distance between the upper wall 14 of the outer vessel body 11 and the bottom wall 23 of the inner vessel body 21 is capable of being set to be comparatively long, and the volume of the enclosed space defined by the outer vessel body 11 and the inner vessel body 21 is capable of being set to be comparatively large. Accordingly, in cases where it is assumed that the volume of the enclosed space is to be set at a predetermined value, the entire size of the outer vessel body 11 and the inner vessel body 21 is capable of being set to be comparatively small. As a result, the size of the blood testing unit is capable of being set to be small.

Also, with the blood testing unit 10, the blood constituent separating membrane 16 is secured to the outer vessel body 11, in which the rubber film 15 acting as the blood introducing section is secured to the upper wall 14, such that the blood constituent separating membrane 16 faces the upper wall 14 of the outer vessel body 11. Therefore, the whole blood 31 having been introduced through the rubber film 15 is capable of being supplied immediately to the blood constituent separating membrane 16.

Further, with the blood testing unit 10, the outer vessel body 11 and the inner vessel body 21 are capable of sliding with respect to each other, while the O-ring 25 fitted onto the outer peripheral wall of the inner vessel body 21 is being in contact with the inner peripheral wall of the outer vessel body 11. Therefore, in cases where the inner vessel body 21 is moved with respect to the outer vessel body 11 in the direction heading away from the outer vessel body 11, and the pressure in the enclosed space is thus set at the negative pressure, the state of the negative pressure is capable of being set more reliably. Also, since the O-ring 25 described above is provided, problems, such as the blood constituents leaking through a gap between the inner vessel body 21 and the outer vessel body 11 to the exterior of the blood testing unit 10, are capable of being prevented.

Furthermore, with the blood testing unit 10, the O-ring 25 of the inner vessel body 21 and the annular engagement section 17 of the outer vessel body 11 are capable of engaging with each other in order to prevent the inner vessel body 21 from separating from the outer vessel body 11. Therefore, problems, such as the inner vessel body 21 and the outer vessel body 11 separating by accident from each other, and the blood constituents leaking from the inner vessel body 21 and the outer vessel body 11 to the exterior, are capable of being prevented. In this embodiment, the O-ring 25 is utilized as the engagement section for engaging with the annular engagement section 17 of the outer vessel body 11. Alternatively, a projecting section may be formed on the outer peripheral surface of the inner vessel body 21 and at a position lower than the position of the O-ring 25 in FIG. 2 and may be utilized as the engagement section of the inner vessel body 21.

Also, with the blood testing unit 10, the plurality of the different kinds of the reagents, each of which is capable of undergoing the reaction with the blood plasma and/or the blood serum and forming the color as a result of the reaction, are supported at the different positions as the glucose detecting spots 24a, 24a and the uric acid detecting spots 24b, 24b on the reagent layer 24. Therefore, in cases where the operation for supplying the blood plasma and/or the blood serum to the reagent layer 24 is performed only one time, the blood plasma and/or the blood serum is capable of being supplied to the plurality of the glucose detecting spots 24a, 24a and the uric acid detecting spots 24b, 24b. Accordingly, the efficiency with which the blood test is performed is capable of being enhanced.

Further, in this embodiment of the blood testing unit 10, the reagent layer 24 is provided with the multiple kinds of the glucose detecting spots 24a, 24a and the uric acid detecting spots 24b, 24b, which are capable of undergoing reactions with different substance contained in the blood plasma and/or blood serum. Also, the blood testing apparatus 40, which is the first embodiment of the blood testing apparatus in accordance with the present invention, is constituted such that the measuring light beams, each of which has a wavelength adapted to one of the reagents contained in the glucose detecting spots 24a, 24a and the uric acid detecting spots 24b, 24b, are irradiated successively to the glucose detecting spots 24a, 24a and the uric acid detecting spots 24b, 24b. Therefore, with the blood testing apparatus 40, the tests with respect to the different substances (in this case, glucose and uric acid) contained in the blood plasma and/or blood serum are capable of being performed quickly. Alternatively, the blood testing apparatus 40 may be constituted such that the measuring light beams are irradiated simultaneously to the multiple kinds of the glucose detecting spots 24a, 24a and the uric acid detecting spots 24b, 24b, and the intensities of the light beams having been reflected from the glucose detecting spots 24a, 24a and the uric acid detecting spots 24b, 24b are measured simultaneously. The alternative constitution of the blood testing apparatus 40 is advantageous for enhancing the efficiency of the blood test.

Also, with the blood testing apparatus 40, the two-dimensional photodetector 50, which detects the image of the reagent layer 24 of the blood testing unit 10, is employed as the means for detecting the optical densities of the glucose detecting spots 24a, 24a and the uric acid detecting spots 24b, 24b. Further, the bar code 24c attached to the reagent layer 24 as illustrated in FIG. 3 is capable of being read out by the two-dimensional photodetector 50. Therefore, in cases where the photo detection signal S, which has been obtained from the two-dimensional photodetector 50, is processed appropriately in the signal processing section 51, and the signal having been obtained from the processing is fed into the displaying section 52, the information concerning the blood testing unit 10, i.e. the production serial number of the blood testing unit 10, the kind of the blood testing unit 10, or the like, which information is represented by the bar code 24c, is capable of being displayed in the displaying section 52. Furthermore, correction of the test results is capable of being made in accordance with correction information with respect to each of production lots of blood testing units 10, 10, . . . , which correction information may be represented by the bar code 24c.

Besides the production serial number of the blood testing unit 10 and the kind of the blood testing unit 10, the information represented by the bar code 24c may also contain information representing the production lot number, information representing the calibration curves, information for correction with respect to interfering substances, information for correction with respect to temperature, information for correction with respect to liquid quantity and the like.

The bar code 24c may be an ordinary one-dimensional bar code. Alternatively, the bar code 24c may be a two-dimensional bar code, or the like. Also, as the mark representing the information concerning the blood testing unit 10, a mark other than the bar code 24c may be employed.

Figure 15:
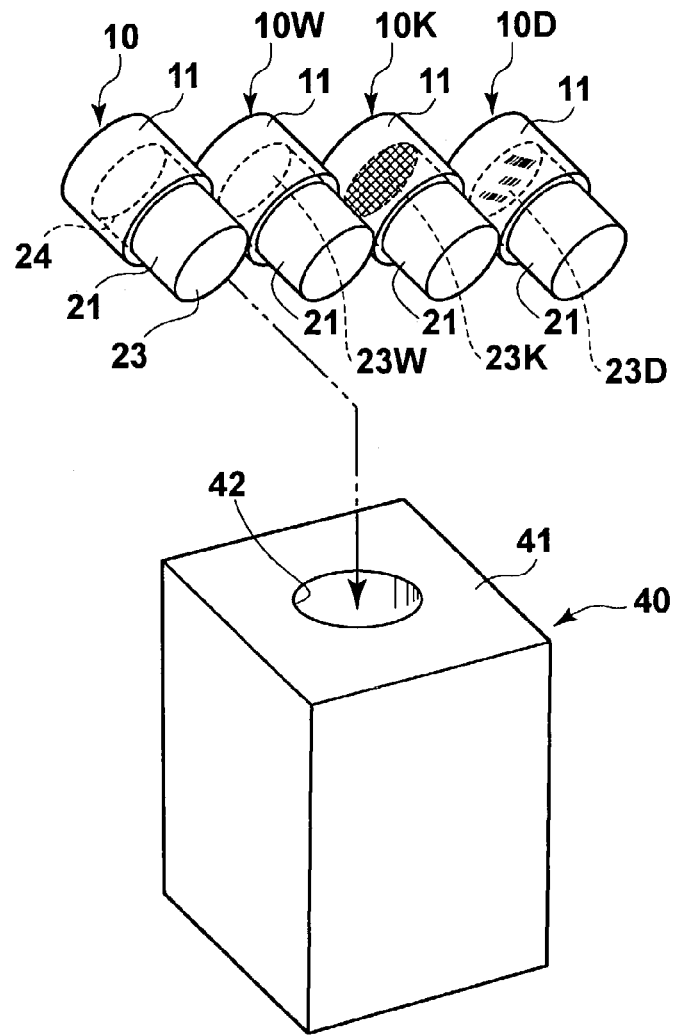
FIG. 15 is a perspective view showing examples of dummy units, which may be utilized in the blood testing apparatus in accordance with the present invention.

In order for an accurate calculation of the optical density to be made from the photo detection signal S, which represents the intensity of the reflected light 43R having been reflected from each of the glucose detecting spots 24a, 24a and the uric acid detecting spots 24b, 24b, in the manner described above, it is necessary to perform a correction operation, wherein values of the photo detection signal S detected in cases where the reflectivity is set at 100% and 0% are obtained, and the photo detection signal S, which represents the intensity of the reflected light 43R having been reflected from each of the glucose detecting spots 24a, 24a and the uric acid detecting spots 24b, 24b, is corrected in accordance with the aforesaid values of the photo detection signal S. FIG. 15 is a perspective view showing method for the correction.

Specifically, in this case, a dummy unit 10W and a dummy unit 10K, each of which has a shape identical with the shape of the blood testing unit 10 and is capable of being accommodated in the unit receiving section 42 of the blood testing apparatus 40, are utilized. The dummy unit 10W comprises an outer vessel body 11W, an inner vessel body 21W, and a white plate 23W, which is located at the position corresponding to the position of the reagent layer 24 of the blood testing unit 10. Also, the dummy unit 10K comprises an outer vessel body 11K, an inner vessel body 21K, and a black plate 23K, which is located at the position corresponding to the position of the reagent layer 24 of the blood testing unit 10. Each of the dummy unit 10W and the dummy unit 10K is accommodated in the unit receiving section 42 of the blood testing apparatus 40, and a photometric operation is performed in the same manner as in the photometric operation for the blood testing unit 10. In this manner, the values of the photo detection signal S detected in cases where the reflectivity is set at 100% and 0% are capable of being obtained. The thus obtained values of the photo detection signal S may be stored in storage means (not shown) and utilized for the correcting operation described above.

As illustrated in FIG. 15, it is also possible to utilize a dummy unit 10D comprising an outer vessel body 11, an inner vessel body 21, and a bar code surface 23D, on which a bar code of the same type as the bar code 24c shown in FIG. 3 has been recorded and which is located at the position corresponding to the position of the reagent layer 24 of the blood testing unit 10. Specifically, for example, one piece of the dummy unit 10D may be accommodated in each pack containing a plurality of blood testing units 10, 10, . . . Also, before each of the blood testing units 10, 10, . . . contained in the pack is used for the blood test, the information represented by the bar code of the dummy unit 10D may be read out and stored in storage means (not shown). In such cases, the information represented by the bar code of the dummy unit 10D may be read from the storage means at the time of the photometric operation for each of the blood testing unit 10, 10, . . . Also, the thus read information may be displayed in the manner described. Alternatively, the results of the blood test may be corrected in accordance with the thus read information.

Figure 16:
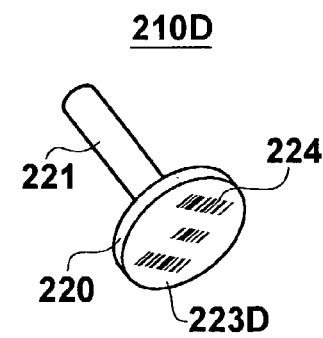
FIG. 16 is a perspective view showing a different example of a dummy unit, which may be utilized in the blood testing apparatus in accordance with the present invention.

Each of the dummy unit 10W, the dummy unit 10K, and the dummy unit 10D need not necessarily have the shape identical with the shape of the blood testing unit 10. For example, a dummy unit 210D having a shape illustrated in FIG. 16 may be utilized. The dummy unit 210D illustrated in FIG. 16 comprises a rod-shaped knob 221 and a circular plate 220, which is secured to one end of the rod-shaped knob 221. The surface of the circular plate 220 constitutes a bar code surface 223D, on which a bar code 224 has been recorded. By way of example, in cases where the dummy unit 210D having the shape different from the shape of the blood testing unit 10 is utilized, the unit receiving section 42 of the blood testing apparatus 40 may be provided with a step-like area for supporting the circular plate 220. In this manner, the dummy unit 210D may be supported in the unit receiving section 42 of the blood testing apparatus 40, such that the position of the bar code surface 223D coincides with the position of the reagent layer 24 of the blood testing unit 10.

In the blood testing apparatus 40 illustrated in FIG. 6, the two-dimensional photodetector 50 constituted of the CCD image sensor, or the like, operates such that the intensity of the reflected light 43R having been reflected from one detecting spot, which is among the glucose detecting spots 24a, 24a and the uric acid detecting spots 24b, 24b of the reagent layer 24, is detected with a plurality of pixels (preferably, with at least 100 pixels). Specifically, with the plurality of the pixels of the two-dimensional photodetector 50 described above, a plurality of independent light intensity detecting operations are performed with respect to a plurality of subareas of the one detecting spot, which is among the glucose detecting spots 24a, 24a and the uric acid detecting spots 24b, 24b of the reagent layer 24. Each of the independent light intensity detecting operations is performed for one of the plurality of the subareas of each of the glucose detecting spots 24a, 24a and the uric acid detecting spots 24b, 24b. Also, the signal processing section 51 performs statistical processing on the results of the plurality of the independent light intensity detecting operations performed with respect to the plurality of the subareas of each of the glucose detecting spots 24a, 24a and the uric acid detecting spots 24b, 24b. From the statistical processing, a light intensity value, which is representative of each of the glucose detecting spots 24a, 24a and the uric acid detecting spots 24b, 24b, is obtained. The thus obtained light intensity value, which is representative of each of the glucose detecting spots 24a, 24a and the uric acid detecting spots 24b, 24b, is taken as the intensity of the reflected light 43R having been reflected from each of the glucose detecting spots 24a, 24a and the uric acid detecting spots 24b, 24b and is utilized for the calculation of the optical density described above.

As the statistical processing described above, for example, processing for calculating a mean value, processing for calculating a median value, or processing for calculating a normal distribution of the detected light intensity values and calculating a mean value of the detected light intensity values, which fall within the range of ±2SD (where SD represents the standard deviation) around a detected light intensity value that is associated with the maximum frequency of occurrence, may be employed.

In the manner described above, the light intensity value, which is representative of each of the glucose detecting spots 24a, 24a and the uric acid detecting spots 24b, 24b, is obtained. Also, the optical density of each detecting spot is calculated in accordance with the thus obtained light intensity value. Therefore, in cases where nonuniformity occurs with the reaction of the reagent with the blood plasma and/or the blood serum within each of the glucose detecting spots 24a, 24a and the uric acid detecting spots 24b, 24b, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately.

As described above, in the blood testing apparatus 40, the region, for which one pixel of the two-dimensional photodetector 50 performs the light intensity detection, is taken as one subarea of each of the glucose detecting spots 24a, 24a and the uric acid detecting spots 24b, 24b. Alternatively, a region, for which a group of a plurality of pixels of the two-dimensional photodetector 50 perform the light intensity detection, may be taken as one subarea of each of the glucose detecting spots 24a, 24a and the uric acid detecting spots 24b, 24b. Specifically, for example, a region, for which a group of four adjacent pixels of the two-dimensional photodetector 50 perform the light intensity detection, may be taken as one subarea of each of the glucose detecting spots 24a, 24a and the uric acid detecting spots 24b, 24b. Also, for example, a mean value of the light intensity values having been detected with the group of the four adjacent pixels may be subjected to the statistical processing described above.

Also, in the blood testing apparatus 40 illustrated in FIG. 6, the measuring light 43 irradiated to each of the glucose detecting spots 24a, 24a and the uric acid detecting spots 24b, 24b is the light component, which has been obtained through light separation so as to have the wavelength corresponding to the reagent contained in each of the glucose detecting spots 24a, 24a and the uric acid detecting spots 24b, 24b. Therefore, the light beams having been reflected from the glucose detecting spots 24a, 24a and the uric acid detecting spots 24b, 24b are capable of being detected by being clearly discriminated from one another. Therefore, the blood tests with respect to a plurality of test purposes are capable of being performed accurately.

Further, in the blood testing apparatus 40 illustrated in FIG. 6, the irradiation of the measuring light 43 to the reagent layer 24 and the detection of the intensity of the reflected light 43R having been reflected from the reagent layer 24 are performed from the side of one surface of the reagent layer 24 opposite to the other surface of the reagent layer 24, on which other surface the blood plasma and/or the blood serum has been supplied to the reagent layer 24. Therefore, the light intensity measuring section 47 for the detection of the reflected light 43R and the light guide member 45 do not interfere with the blood constituent separating membrane 16 for supplying the blood plasma and/or the blood serum. Accordingly, flexibility in layout of the light intensity measuring section 47 and the light guide member 45 is capable of being kept high. Particularly, in this case, the reagent layer 24 is accommodated in the closed vessel constituted of the outer vessel body 11 and the inner vessel body 21, and the layout of the light intensity measuring section 47 and the light guide member 45 is ordinarily not easy. Therefore, the effect of keeping the flexibility in layout of the light intensity measuring section 47 and the light guide member 45 high is markedly advantageous in practice. The effect described above is also obtained with the blood testing apparatuses shown in FIG. 6, FIG. 8, FIG. 9, and FIG. 10, which will be described later.

Figure 7:
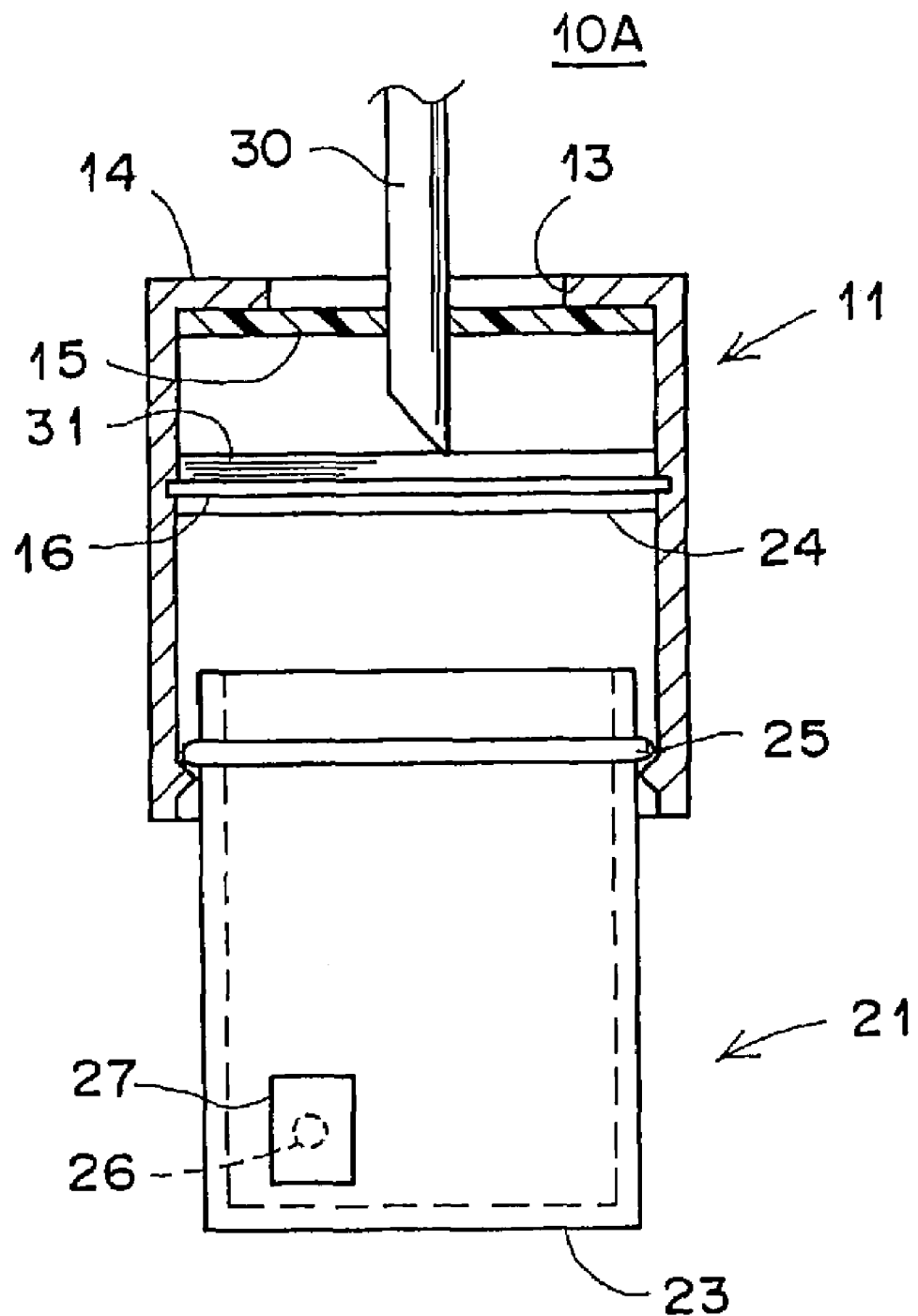
FIG. 7 is a partially cutaway side view showing a second embodiment of the blood testing unit in accordance with the present invention.

A blood testing unit 10A, which is a second embodiment of the blood testing unit in accordance with the present invention, will be described hereinbelow with reference to FIG. 7. In FIG. 7 (and those that follow), similar elements are numbered with the same reference numerals with respect to FIG. 1 to FIG. 6.

The blood testing unit 10A illustrated in FIG. 7 is constituted basically in the same manner as that in the blood testing unit 10 shown in FIG. 1 to FIG. 6, except that the reagent layer 24 is not formed on the side of an inner vessel body 21 and is formed on the side of an outer vessel body 11. The reagent layer 24 is formed such that the reagent layer 24 is in contact with the back surface of the blood constituent separating membrane 16 located within the outer vessel body 11, which back surface is opposite to the surface that faces the rubber film 15.

In cases where the blood testing unit 10A constituted in the manner described above is utilized, the blood test is capable of being performed basically in the same manner as that described above by use of the blood testing apparatus 40 shown in FIG. 5 and FIG. 6. However, in this case, after the whole blood 31 has been introduced into the blood testing unit 10A, the outer vessel body 11 need not necessarily be pushed toward the inner vessel body 21, and the blood plasma and/or the blood serum having been separated by the blood constituent separating membrane 16 from the whole blood 31 is capable of spreading through the reagent layer 24. Specifically, with the blood testing unit 10A, the supply of the blood plasma and/or the blood serum to the reagent layer 24 is performed more quickly than with the blood testing unit 10 described above.

Figure 8:
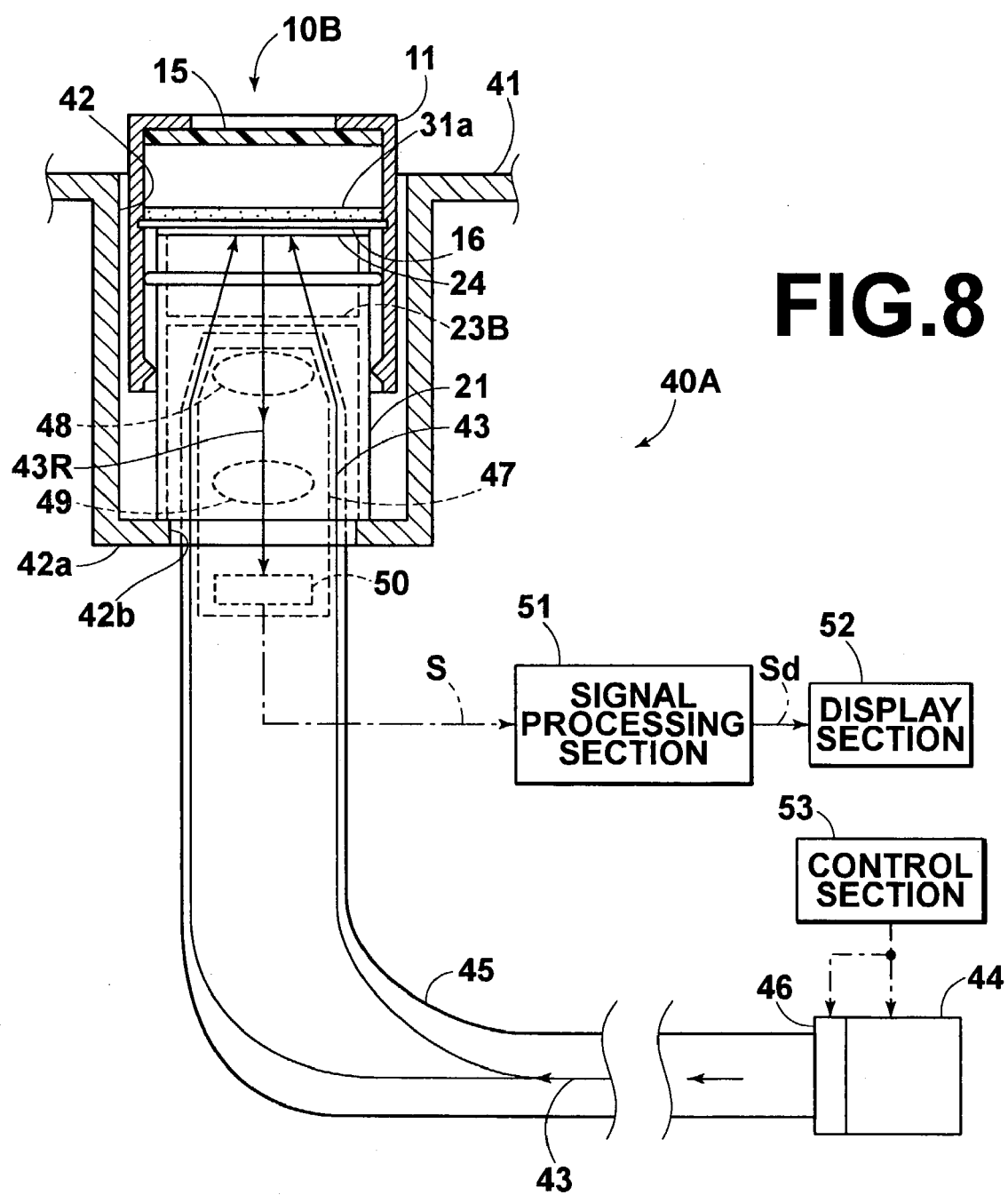
FIG. 8 is a partially cutaway side view showing a third embodiment of the blood testing unit in accordance with the present invention and a second embodiment of the blood testing apparatus in accordance with the present invention.

A blood testing unit 10B, which is a third embodiment of the blood testing unit in accordance with the present invention, and a blood testing apparatus 40A, which is a second embodiment of the blood testing apparatus in accordance with the present invention, will be described hereinbelow with reference to FIG. 8. The blood testing unit 10B illustrated in FIG. 8 is constituted basically in the same manner as that in the blood testing unit 10 shown in FIG. 1 to FIG. 6, except that a bottom wall 23B of an inner vessel body 21B is not formed at an end portion of the inner vessel body 21B and is formed at an intermediate area of the inner vessel body 21B. Also, the blood testing apparatus 40A illustrated in FIG. 8 is constituted basically in the same manner as that in the blood testing apparatus 40 shown in FIG. 6, except that a light guide member 45 is formed such that a light radiating end portion of the light guide member 45 is capable of passing through an opening 42b of the bottom plate of the unit receiving section 42 and entering into the inner vessel body 21 of the blood testing unit 10B. A light radiating end face of the light guide member 45 comes into contact with the bottom wall 23B of the inner vessel body 21. Therefore, the distance between the objective lens 48 of the light intensity measuring section 47 and the reagent layer 24, the distance between the image forming lens 49 of the light intensity measuring section 47 and the reagent layer 24, and the distance between the two-dimensional photodetector 50 of the light intensity measuring section 47 and the reagent layer 24 are kept at predetermined values.

In cases where the blood testing unit 10B and the blood testing apparatus 40A having the constitutions described above are utilized, the blood test is capable of being performed basically in the same manner as that in cases where the blood testing unit 10 and the blood testing apparatus 40 shown in FIG. 6 are utilized.

In the blood testing apparatus 40A, similar to the blood testing apparatus 40 illustrated in FIG. 6, the two-dimensional photodetector 50 constituted of the CCD image sensor, or the like, operates such that the intensity of the reflected light having been reflected from one detecting spot, which is among the glucose detecting spots 24a, 24a and the uric acid detecting spots 24b, 24b of the reagent layer 24, is detected with a plurality of pixels (preferably, with at least 100 pixels). Specifically, with the plurality of the pixels of the two-dimensional photodetector 50 described above, a plurality of independent light intensity detecting operations are performed with respect to a plurality of subareas of the one detecting spot, which is among the glucose detecting spots 24a, 24a and the uric acid detecting spots 24b, 24b of the reagent layer 24. Also, the signal processing section 51 performs statistical processing on the results of the plurality of the independent light intensity detecting operations performed with respect to the plurality of the subareas of each of the glucose detecting spots 24a, 24a and the uric acid detecting spots 24b, 24b. From the statistical processing, a light intensity value, which is representative of each of the glucose detecting spots 24a, 24a and the uric acid detecting spots 24b, 24b, is obtained. The thus obtained light intensity value, which is representative of each of the glucose detecting spots 24a, 24a and the uric acid detecting spots 24b, 24b, is taken as the intensity of the reflected light 43R having been reflected from each of the glucose detecting spots 24a, 24a and the uric acid detecting spots 24b, 24b and is utilized for the calculation of the optical density described above.

As the statistical processing described above, for example, processing for calculating a mean value, processing for calculating a median value, or processing for calculating a normal distribution of the detected light intensity values and calculating a mean value of the detected light intensity values, which fall within the range of ±2SD (where SD represents the standard deviation) around a detected light intensity value that is associated with the maximum frequency of occurrence, may be employed.

In the manner described above, the light intensity value, which is representative of each of the glucose detecting spots 24a, 24a and the uric acid detecting spots 24b, 24b, is obtained. Also, the optical density of each detecting spot is calculated in accordance with the thus obtained light intensity value. Therefore, in cases where nonuniformity occurs with the reaction of the reagent with the blood plasma and/or the blood serum within each of the glucose detecting spots 24a, 24a and the uric acid detecting spots 24b, 24b, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately.

Figure 9:
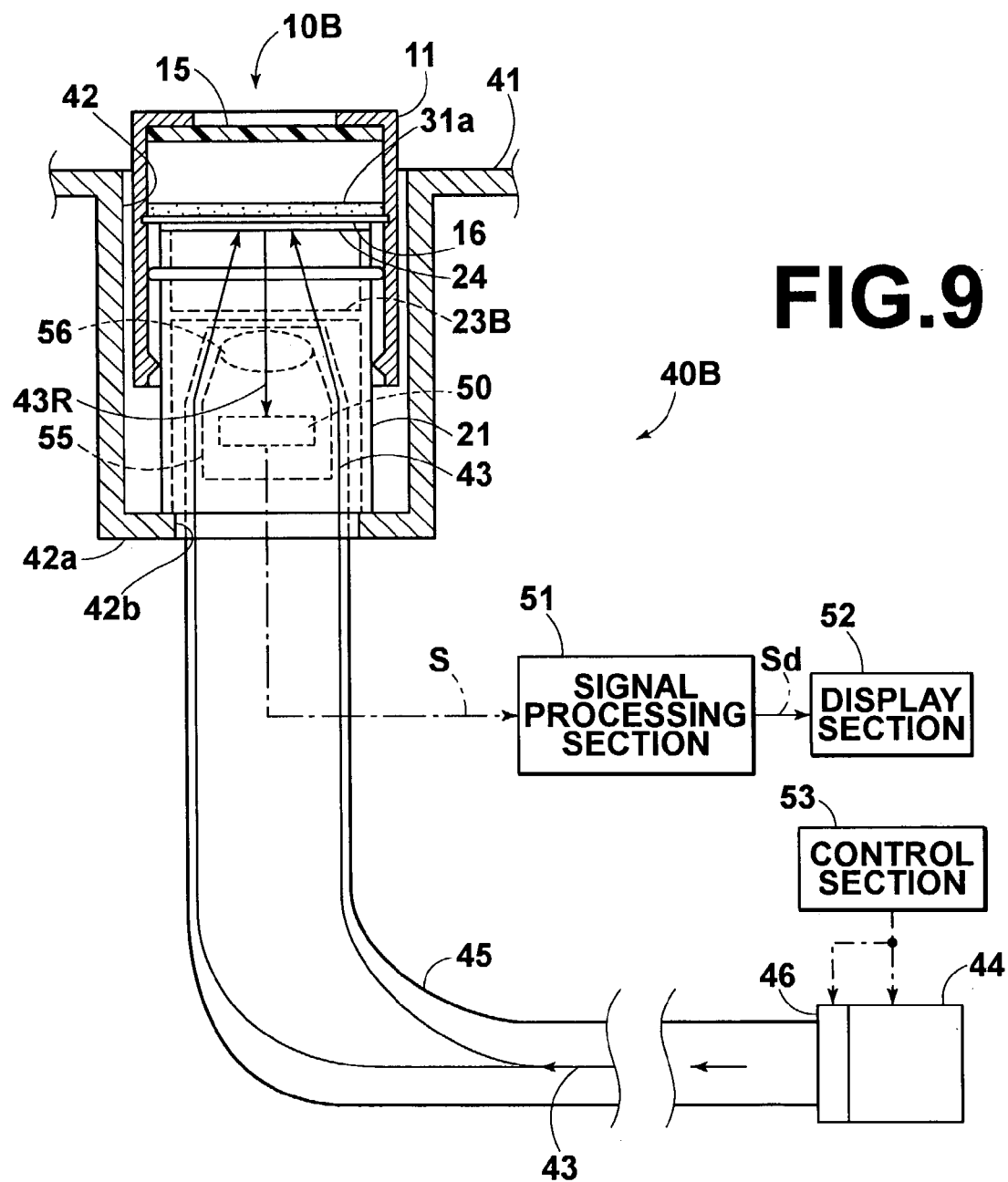
FIG. 9 is a partially cutaway side view showing a third embodiment of the blood testing apparatus in accordance with the present invention.

A blood testing apparatus 40B, which is a third embodiment of the blood testing apparatus in accordance with the present invention, will be described hereinbelow with reference to FIG. 9. The blood testing apparatus 40B illustrated in FIG. 9 is constituted basically in the same manner as that in the blood testing apparatus 40A shown in FIG. 8, except for a constitution of a light intensity measuring section 55. Specifically, the light intensity measuring section 55 comprises the two-dimensional photodetector 50 and an image forming lens 56. Also, in the blood testing apparatus 40B, the light radiating end face of the light guide member 45A comes into contact with the bottom wall 23B of the inner vessel body 21B. Therefore, the distance between the image forming lens 56 of the light intensity measuring section 55 and the reagent layer 24 and the distance between the two-dimensional photodetector 50 of the light intensity measuring section 55 and the reagent layer 24 are kept at predetermined values. In the blood testing apparatus 40B, as the blood testing unit 10B, the blood testing unit 10B illustrated in FIG. 8 is utilized.

In cases where the blood testing unit 10B and the blood testing apparatus 40B having the constitutions described above are utilized, the blood test is capable of being performed basically in the same manner as that in cases where the blood testing unit 10 and the blood testing apparatus 40 shown in FIG. 6 are utilized.

In the blood testing apparatus 40B, similar to the blood testing apparatus 40 illustrated in FIG. 6, the two-dimensional photodetector 50 constituted of the CCD image sensor, or the like, operates such that the intensity of the reflected light having been reflected from one detecting spot, which is among the glucose detecting spots 24a, 24a and the uric acid detecting spots 24b, 24b of the reagent layer 24, is detected with a plurality of pixels (preferably, with at least 100 pixels). Specifically, with the plurality of the pixels of the two-dimensional photodetector 50 described above, a plurality of independent light intensity detecting operations are performed with respect to a plurality of subareas of the one detecting spot, which is among the glucose detecting spots 24a, 24a and the uric acid detecting spots 24b, 24b of the reagent layer 24. Also, the signal processing section 51 performs statistical processing on the results of the plurality of the independent light intensity detecting operations performed with respect to the plurality of the subareas of each of the glucose detecting spots 24a, 24a and the uric acid detecting spots 24b, 24b.

From the statistical processing, a light intensity value, which is representative of each of the glucose detecting spots 24a, 24a and the uric acid detecting spots 24b, 24b, is obtained. The thus obtained light intensity value, which is representative of each of the glucose detecting spots 24a, 24a and the uric acid detecting spots 24b, 24b, is taken as the intensity of the reflected light 43R having been reflected from each of the glucose detecting spots 24a, 24a and the uric acid detecting spots 24b, 24b and is utilized for the calculation of the optical density described above.

As the statistical processing described above, for example, processing for calculating a mean value, processing for calculating a median value, or processing for calculating a normal distribution of the detected light intensity values and calculating a mean value of the detected light intensity values, which fall within the range of ±2SD (where SD represents the standard deviation) around a detected light intensity value that is associated with the maximum frequency of occurrence, may be employed.

In the manner described above, the light intensity value, which is representative of each of the glucose detecting spots 24a, 24a and the uric acid detecting spots 24b, 24b, is obtained. Also, the optical density of each detecting spot is calculated in accordance with the thus obtained light intensity value. Therefore, in cases where nonuniformity occurs with the reaction of the reagent with the blood plasma and/or the blood serum within each of the glucose detecting spots 24a, 24a and the uric acid detecting spots 24b, 24b, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately.

Figure 10:
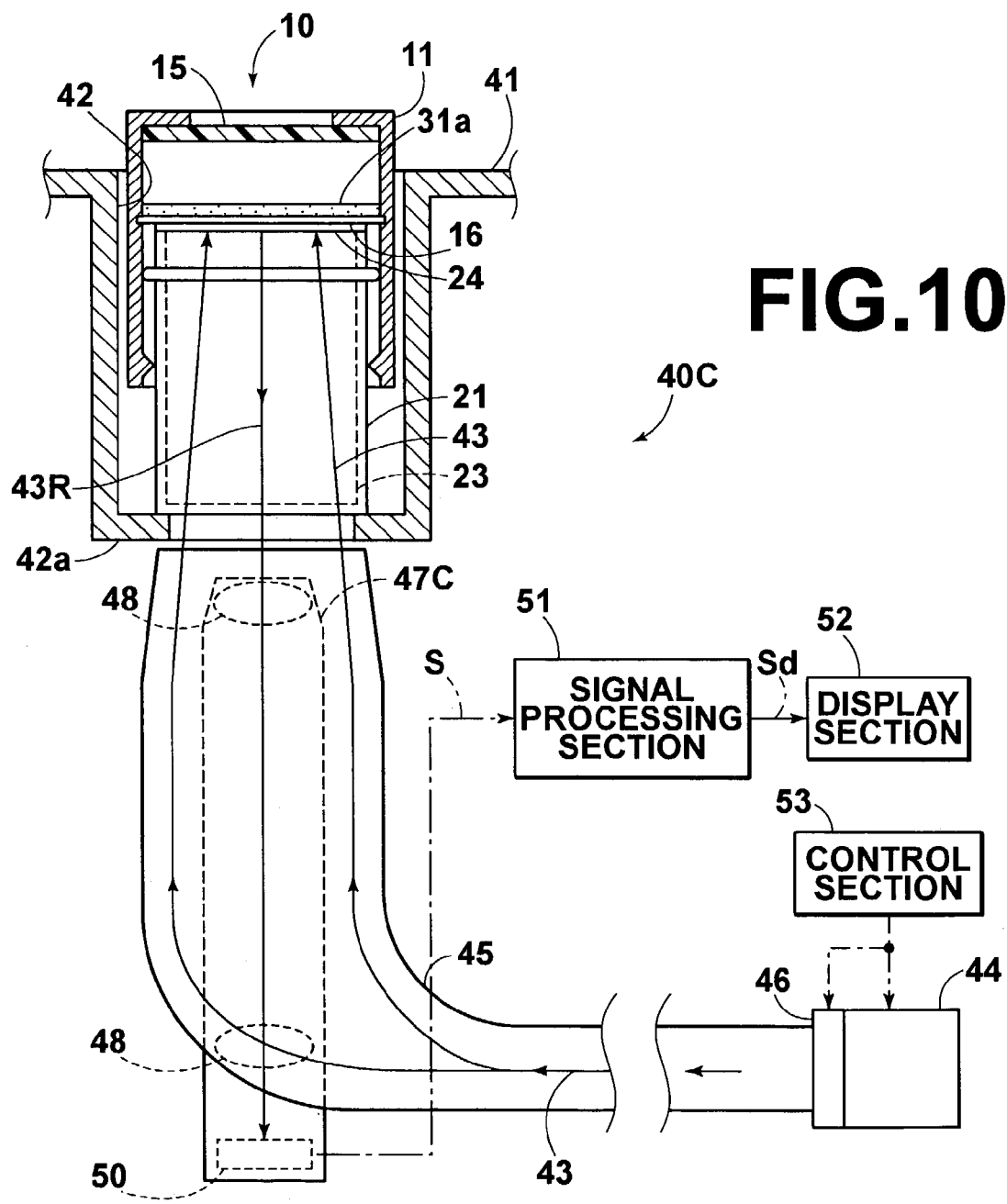
FIG. 10 is a partially cutaway side view showing a fourth embodiment of the blood testing apparatus in accordance with the present invention.

A blood testing apparatus 40c, which is a fourth embodiment of the blood testing apparatus in accordance with the present invention, will be described hereinbelow with reference to FIG. 10. The blood testing apparatus 40C illustrated in FIG. 10 is constituted basically in the same manner as that in the blood testing apparatus 40 shown in FIG. 6, except that a light intensity measuring section 47C has a shape longer than the shape of the light intensity measuring section 47, and a rear end portion of the light intensity measuring section 47C extends from the light guide member 45 to the exterior. In the light intensity measuring section 47C, as the blood testing unit 10, the blood testing unit 10 illustrated in FIG. 6 is utilized.

In cases where the blood testing apparatus 40C constituted in the manner described above is utilized, the blood test is capable of being performed basically in the same manner as that in cases where the blood testing apparatus 40 shown in FIG. 6 is utilized.

In the blood testing apparatus 40C, similar to the blood testing apparatus 40 illustrated in FIG. 6, the two-dimensional photodetector 50 constituted of the CCD image sensor, or the like, operates such that the intensity of the reflected light having been reflected from one detecting spot, which is among the glucose detecting spots 24a, 24a and the uric acid detecting spots 24b, 24b of the reagent layer 24, is detected with a plurality of pixels (preferably, with at least 100 pixels). Specifically, with the plurality of the pixels of the two-dimensional photodetector 50 described above, a plurality of independent light intensity detecting operations are performed with respect to a plurality of subareas of the one detecting spot, which is among the glucose detecting spots 24a, 24a and the uric acid detecting spots 24b, 24b of the reagent layer 24. Also, the signal processing section 51 performs statistical processing on the results of the plurality of the independent light intensity detecting operations performed with respect to the plurality of the subareas of each of the glucose detecting spots 24a, 24a and the uric acid detecting spots 24b, 24b. From the statistical processing, a light intensity value, which is representative of each of the glucose detecting spots 24a, 24a and the uric acid detecting spots 24b, 24b, is obtained. The thus obtained light intensity value, which is representative of each of the glucose detecting spots 24a, 24a and the uric acid detecting spots 24b, 24b, is taken as the intensity of the reflected light 43R having been reflected from each of the glucose detecting spots 24a, 24a and the uric acid detecting spots 24b, 24b and is utilized for the calculation of the optical density described above.

As the statistical processing described above, for example, processing for calculating a mean value, processing for calculating a median value, or processing for calculating a normal distribution of the detected light intensity values and calculating a mean value of the detected light intensity values, which fall within the range of ±2SD (where SD represents the standard deviation) around a detected light intensity value that is associated with the maximum frequency of occurrence, may be employed.

In the manner described above, the light intensity value, which is representative of each of the glucose detecting spots 24a, 24a and the uric acid detecting spots 24b, 24b, is obtained. Also, the optical density of each detecting spot is calculated in accordance with the thus obtained light intensity value. Therefore, in cases where nonuniformity occurs with the reaction of the reagent with the blood plasma and/or the blood serum within each of the glucose detecting spots 24a, 24a and the uric acid detecting spots 24b, 24b, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately.

Figure 11:
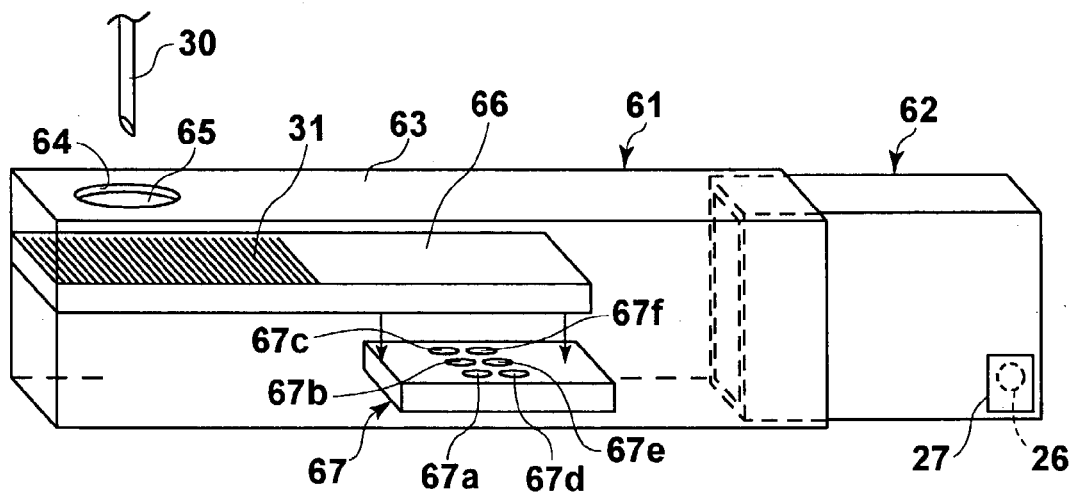
FIG. 11 is a perspective view showing a fourth embodiment of the blood testing unit in accordance with the present invention.

A blood testing unit 60, which is a fourth embodiment of the blood testing unit in accordance with the present invention, will be described hereinbelow with reference to FIG. 11. The blood testing unit 60 illustrated in FIG. 11 comprises a rectangular box-shaped outer vessel body 61, which has a bottom wall at an end portion and is made from a transparent member. The blood testing unit 60 also comprises a rectangular box-shaped inner vessel body 62, which is combined with the outer vessel body 61 for slide movement within the outer vessel body 61. The blood testing unit 60 further comprises a rubber film 65, which acts as the blood introducing section and closes a circular opening 64 formed through a side wall 63 of the outer vessel body. The blood testing unit 60 still further comprises a plate-shaped blood constituent separating membrane 66, which is located within the outer vessel body 61 so as to extend along the axial direction of the outer vessel body 61. The blood testing unit 60 also comprises a plate-shaped reagent layer 67, which is secured to a lower surface of the blood constituent separating membrane 66 in FIG. 11. In FIG. 11, as an aid in facilitating the explanation, the reagent layer 67 is illustrated at a position spaced away from the blood constituent separating membrane 66.

As in the cases of the outer vessel body 11 and the inner vessel body 21 of the blood testing unit 10 illustrated in FIG. 6, the outer vessel body 61 and the inner vessel body 62 of the blood testing unit 60 define an enclosed space at the interior. Also, in cases where the inner vessel body 62 is moved in the direction heading away from the outer vessel body 61 (i.e., toward the right-hand side in FIG. 11), the pressure in the enclosed space is set at the negative pressure.

The blood constituent separating membrane 66 is constituted basically in the manner as that in the blood constituent separating membrane 16 of the blood testing unit 10 illustrated in FIG. 6, except that the blood constituent separating membrane 66 has a thickness larger than the thickness of the blood constituent separating membrane 16 and has the plate-like shape.

By way of example, the reagent layer 67 comprises a plate-shaped nitrocellulose porous membrane, which has a pore diameter of 0.45 μm and acts as the support. Also, detecting spots 67a, 67b, 67c, 67d, 67e and 67f, each of which contain one of a plurality of different kinds (by way of example, six kinds) of reagents, have been formed with a spotting process on the nitrocellulose porous membrane. Each of the plurality of the different kinds of the reagents is capable of undergoing a reaction with one of a plurality of different substances contained in the blood plasma and/or the blood serum and is capable of forming a color as a result of the reaction. As described above, the reagent layer 67 is secured to the blood constituent separating membrane 66. Therefore, the reagent, layer 67 also extends along the axial direction of the outer vessel body 61.

How a blood test is performed by use of the blood testing unit 60 described above will be described hereinbelow. Firstly, how an operation for taking a blood sample is performed will be described hereinbelow. In order for the blood sample to be taken, the inner vessel body 62 is operated in the manner described above, and the pressure within the enclosed space in the blood testing unit 60 is thus set at the negative pressure. In this state, one tip of the blood sampling needle 30, whose other tip has been stuck in, for example, the upper arm of a human body, is stuck through the rubber film 65 of the outer vessel body 61 into the enclosed space described above. As a result, since the pressure within the enclosed space has been set at the negative pressure, the whole blood 31 passes through the blood sampling needle 30 and is thus introduced into the enclosed space. As illustrated in FIG. 11, the whole blood 31 spreads over the blood constituent separating membrane 66. Solid constituents of the whole blood 31 are caught on the surface of the blood constituent separating membrane 66, and the blood plasma and/or the blood serum passes through the blood constituent separating membrane 66. The blood plasma and/or the blood serum, which has passed through the blood constituent separating membrane 66, spreads over the reagent layer 67. Each of the detecting spots 67a to 67f of the reagent layer 67 undergoes the reaction with one of the specific substances, which are contained in the blood plasma and/or the blood serum and are to be tested. As a result of the reaction, each of the detecting spots 67a to 67f forms the color.

The inner vessel body 62 of the blood testing unit 60 is provided with the air introducing aperture 26, and the sealing member 27 for closing the air introducing aperture 26 is adhered to the inner vessel body 62. Therefore, with the air introducing aperture 26 and the sealing member 27, the same effects as those described above are capable of being obtained.

Figure 12:
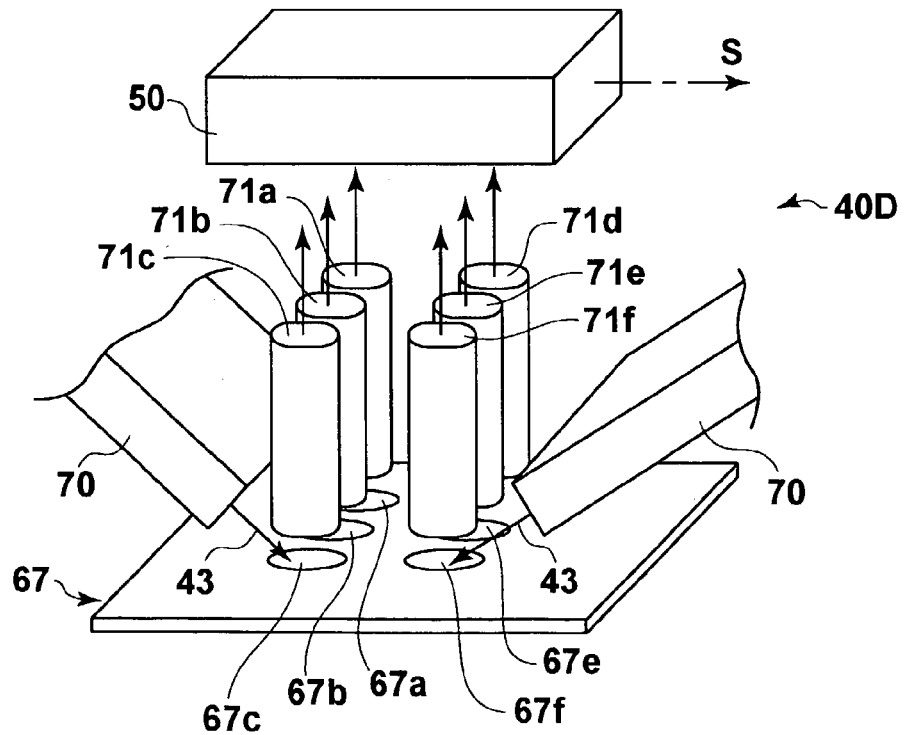
FIG. 12 is a perspective view showing a major part of a fifth embodiment of the blood testing apparatus in accordance with the present invention.

How the optical densities of the detecting spots 67a to 67f are measured will be described hereinbelow. FIG. 12 is a perspective view showing a major part of a blood testing apparatus 40D, which is a fifth embodiment of the blood testing apparatus in accordance with the present invention. In the blood testing apparatus 40D, the blood testing unit 60 is subjected to the photometric operation. As illustrated in FIG. 12, the blood testing apparatus 40D comprises a pair of light guide member 70, 70 for irradiating the measuring light 43 to the detecting spots 67a, 67b, 67c, 67d, 67e, and 67f of the reagent layer 67 from the side of a back surface (i.e., the lower surface in FIG. 11) of the reagent layer 67 of the blood testing unit 60. The blood testing apparatus 40D also comprises six distributed index lenses 71a, 71b, 71c, 71d, 71e, and 71f, which are located at positions corresponding to the positions of the detecting spots 67a, 67b, 67c, 67d, 67e, and 67f. The blood testing apparatus 40D further comprises the two-dimensional photodetector 50, such as a CCD image sensor, which is located so as to stand facing all of the distributed index lenses 71a, 71b, 71c, 71d, 71e, and 71f.

One side wall of the outer vessel body 61 of the blood testing unit 60 intervenes between the blood testing apparatus 40D and the reagent layer 67. In FIG. 12, as an aid in facilitating the explanation, the one side wall of the outer vessel body 61 is not shown.

In the blood testing apparatus 40D having the constitution described above, when the measuring light 43 is irradiated to the reagent layer 67, light beams having been reflected from the detecting spots 67a, 67b, 67c, 67d, 67e, and 67f of the reagent layer 67 are efficiently collected respectively by the distributed index lenses 71a, 71b, 71c, 71d, 71e, and 71f. Therefore, the intensity of the reflected light beam is measured with respect to each of the distributed index lenses 71a to 71f, i.e. with respect to each of the detecting spots 67a to 67f. Accordingly, with the blood testing apparatus 40D, the optical density of each of the detecting spots 67a to 67f having formed the colors is capable of being detected in accordance with the photo detection signal S, which is obtained from the two-dimensional photodetector 50.

In order for the concentrations of the specific substances, which have reacted with the detecting spots 67a to 67f, to be calculated from the optical densities of the detecting spots 67a to 67f, whose optical densities change with the passage of time, basically the same technique as the technique utilizing the calibration curves, which technique is employed in the blood testing apparatus 40 of FIG. 6, may be employed.

Also, in the blood testing apparatus 40D, described above, the irradiation of the measuring light 43 to the reagent layer 67 and the detection of the intensities of the light beams having been reflected from the reagent layer 67 are performed from the side of the back surface of the reagent layer 67 of the blood testing unit 60 opposite to the other surface of the reagent layer 67, which other surface faces the blood constituent separating membrane 66 for supplying the blood plasma and/or the blood serum to the reagent layer 67 as illustrated in FIG. 11. Therefore, the light guide member 70, 70, the distributed index lenses 71a to 71f, and the two-dimensional photodetector 50 do not interfere with the blood constituent separating membrane 66. Accordingly, the layout of the light guide member 70, 70, the distributed index lenses 71a to 71f, and the two-dimensional photodetector 50 becomes easy. Particularly, in the blood testing apparatus 40D, wherein the distributed index lenses 71a to 71f are located such that each of the distributed index lenses 71a to 71f corresponds to one of the detecting spots 67a to 67f, the flexibility in layout of the distributed index lenses 71a to 71f is ordinarily not high. Therefore, the effect of keeping the layout of the light guide member 70, 70, the distributed index lenses 71a to 71f, and the two-dimensional photodetector 50 easy is markedly advantageous in practice. The effect described above is also obtained with the blood testing apparatuses shown in FIG. 13, FIG. 18, FIG. 22, which will be described later.

Further, with the blood testing apparatus 40D, the optical detection signal S, which is outputted from the two-dimensional photodetector 50, is subjected to the statistical processing in the same manner as that in the signal processing section 51 of the blood testing apparatus 40 illustrated in FIG. 6. In the manner described above, the light intensity value, which is representative of each of the detecting spots 67a to 67f is obtained. Also, the optical density of each detecting spot 67a to 67f is calculated in accordance with the thus obtained light intensity value. Therefore, in cases where nonuniformity occurs with the reaction of the reagent with the blood plasma and/or the blood serum within each of the detecting spots 67a to 67f, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately.

Further, in the blood testing apparatus 40D, the distributed index lenses 71a to 71f are located such that each of the distributed index lenses 71a to 71f faces one of the detecting spots 67a to 67f. Therefore, problems, such as the measuring light having been scattered by areas of the reagent layer 67 other than the detecting spots 67a to 67f being detected by the two-dimensional photodetector 50, and the accuracy of the blood test being affected adversely, are capable of being prevented.

Experiments were conducted for confirmation of the effect described above. In the experiments, an aqueous Bromophenol Blue solution acting as a reagent was spotted onto a nitrocellulose membrane, and a reagent layer was thus formed. Diameters of detecting spots were set at 500 µm, and pitches of the detecting spots were set at 1 mm, such that the detecting spots having formed colors may be arrayed at predetermined intervals. In this manner, four detecting spots (i.e., two detecting spots arrayed in the vertical direction x two detecting spots arrayed in the horizontal direction) were formed. Halogen lamps were employed as light sources for producing measuring light beams, and R-60 (supplied by Hoya Corp.) was employed as optical filters. By use of the halogen lamps and the optical filters, the measuring light beams were irradiated to the detecting spots described above. Light beams having been reflected from the detecting spots were collected by distributed index lenses, each of which was located with respect to one of the detecting spots, and the intensities of the reflected light beams were detected. A mean value of the thus detected intensities of the light beams having been reflected from the detecting spots was taken as 100. Also, an experiment was conducted by use of a unit for experiment, in which the areas of the reagent layer 67 other than the detecting spots 67a to 67f had been set as black areas. In the experiment using the unit for experiment, a mean value of the detected intensities of the light beams having been reflected from the detecting spots was equal to 100. If the light collecting optical system comprising the distributed index lenses also collected the light having been scattered from the areas of the reagent layer 67 other than the detecting spots 67a to 67f, the mean value of the detected intensities of the light beams having been reflected from the detecting spots would be smaller than 100 in the experiment using the unit for experiment. However, since the mean value of the detected intensities of the light beams having been reflected from the detecting spots was equal to 100 in the experiment using the unit for experiment, it was confirmed that the light collecting optical system did not collect the scattered light. The effect described above is also obtained in cases where a one-dimensional photodetector is employed as the photodetector in lieu of the two-dimensional photodetector 50.

Figure 13:
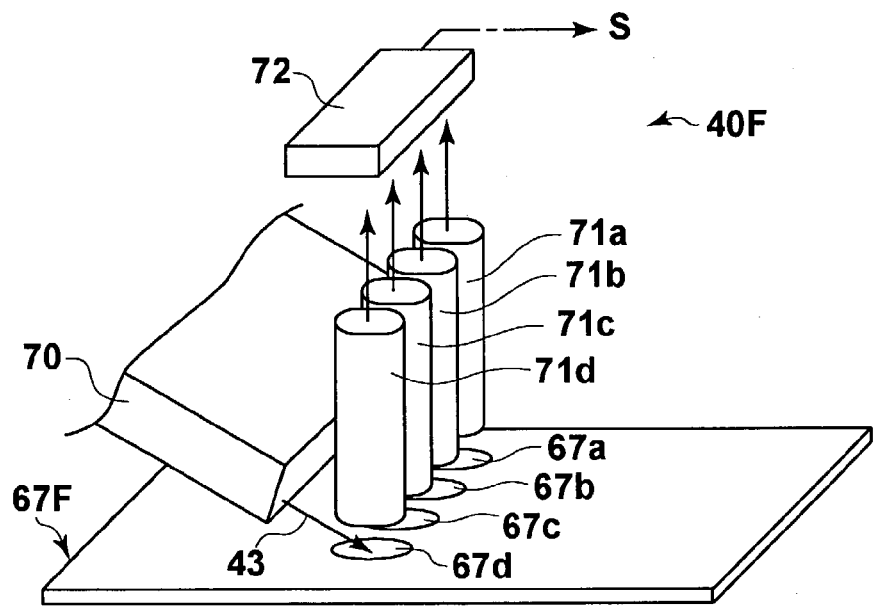
FIG. 13 is a perspective view showing a major part of a sixth embodiment of the blood testing apparatus in accordance with the present invention.

A blood testing apparatus 40F, which is a sixth embodiment of the blood testing apparatus in accordance with the present invention, will be described hereinbelow with reference to FIG. 13. The blood testing apparatus 40F illustrated in FIG. 13 is constituted for the cases where a reagent layer 67F is provided with a plurality of (by way of example, four) detecting spots 67a, 67b, 67c, and 67d, which are arrayed in one row. The blood testing apparatus 40F is constituted basically in the same manner as that in the blood testing apparatus 40D illustrated in FIG. 12, except that four distributed index lenses 71a, 71b, 71c, and 71d are arrayed in one row, and a one-dimensional photodetector 72 constituted of a CCD linear sensor, or the like, is employed as the photodetector.

In the blood testing apparatus 40F, when the measuring light 43 is irradiated to the reagent layer 67F, the light beams having been reflected from the detecting spots 67a, 67b, 67c, and 67d of the reagent layer 67F are efficiently collected respectively by the distributed index lenses 71a, 71b, 71c, and 71d. Therefore, the intensity of the reflected light beam is measured with respect to each of the distributed index lenses 71a to 71d, i.e. with respect to each of the detecting spots 67a to 67d. Accordingly, with the blood testing apparatus 40F, the optical density of each of the detecting spots 67a to 67d having formed the colors is capable of being detected in accordance with the photo detection signal S, which is obtained from the one-dimensional photodetector 72.

In order for the concentrations of the specific substances, which have reacted with the detecting spots 67a to 67d, to be calculated from the optical densities of the detecting spots 67a to 67d, whose optical densities change with the passage of time, basically the same technique as the technique utilizing the calibration curves, which technique is employed in the blood testing apparatus 40 of FIG. 6, may be employed.

Further, with the blood testing apparatus 40F, the optical detection signal S, which is outputted from the one-dimensional photodetector 72, is subjected to the statistical processing in the same manner as that in the signal processing section 51 of the blood testing apparatus 40 illustrated in FIG. 6. In the manner described above, the light intensity value, which is representative of each of the detecting spots 67a to 67f, is obtained. Also, the optical density of each detecting spot 67a to 67f is calculated in accordance with the thus obtained light intensity value. Therefore, in cases where nonuniformity occurs with the reaction of the reagent with the blood plasma and/or the blood serum within each of the detecting spots 67a to 67f, or in cases where fine dust, or the like, is present within each of the detecting spots, adverse effects of specific results of the light intensity detection due to the nonuniformity in reaction, the fine dust, or the like, are capable of being eliminated, and the blood test is capable of being performed accurately. In cases where the blood testing apparatus 40H, which will be described hereinbelow, is employed, the effects described above are similarly obtained.

Figure 14:
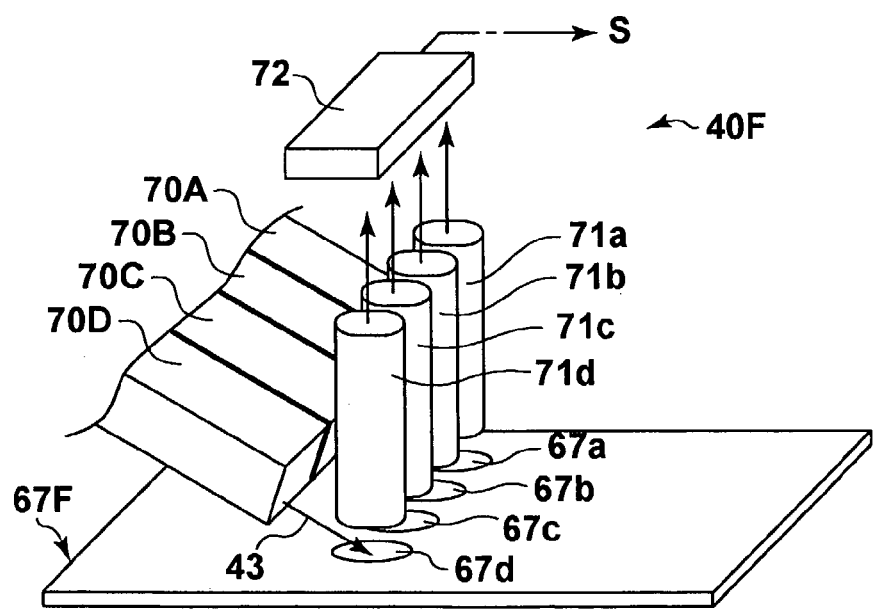
FIG. 14 is a perspective view showing a major part of a seventh embodiment of the blood testing unit in accordance with the present invention.

A blood testing apparatus 40H, which is a seventh embodiment of the blood testing apparatus in accordance with the present invention, will be described hereinbelow with reference to FIG. 14. The blood testing apparatus 40H illustrated in FIG. 14 is constituted basically in the same manner as that in the blood testing apparatus 40F illustrated in FIG. 13, except that, in lieu of the single, comparatively large light guide member 70, four light guide members 70a, 70b, 70c, and 70d are utilized. The four light guide members 70a, 70b, 70c, and 70d irradiate the measuring light beams 43, 43, . . . respectively to the four detecting spots 67a, 67b, 67c, and 67d of the reagent layer 67F.

The light guide members 70a, 70b, 70c, and 70d constitute four independent light sending systems. Therefore, with the constitution illustrated in FIG. 14, the measuring light beams, which have been separated from one another such that each of the measuring light beams has a wavelength adapted to one of the reagents contained in the four detecting spots 67a, 67b, 67c, and 67d, are capable of being irradiated to the detecting spots 67a, 67b, 67c, and 67d as the independent measuring light irradiating operations. Accordingly, the accuracy of the blood test is capable of being enhanced.

Elements constituting the embodiment of the blood testing apparatus in accordance with the present invention will hereinbelow be described in more detail.

As the light source for producing the measuring light, besides the aforesaid light emitting diode for producing the monochromatic light or the white light, a white light source, such as a halogen lamp or a xenon lamp, may be employed. Also, as the means for converting the measuring light into monochromatic light, an optical filter, which transmits the light having wavelengths falling within a range of approximately a center wavelength ±3 nm, is capable of being utilized appropriately. Alternatively, a filter having comparatively bad monochromatic characteristics and transmitting the light having wavelengths falling within a range of approximately a center wavelength ±30 nm, which wavelengths fall within the range of the absorption wavelengths of the reagents having formed the colors, may be utilized. As another alternative, a light emitting diode, a semiconductor laser, or the like, which has good monochromatic characteristics and transmits only the light having a wavelength falling within the range of the absorption wavelengths of the reagents having formed the colors, may be utilized alone without being combined with a filter.

As the means for detecting the light having been reflected from the reagent layer, besides the aforesaid CCD detector, means capable of performing simultaneous multiple-point detection, such as a photodiode array or an optical multianalyzer, may be utilized. Alternatively, a plurality of devices, each of which is capable of performing single-point detection, such as photomultipliers, may be arrayed and utilized.

In order to obtain the photo detection signal S in cases where the reflectivity of the reagent layer with respect to the measuring light is 0%, besides the dummy unit 10K shown in FIG. 15, one of various other means capable of blocking the measuring light, which travels toward the reagent layer, or the light, which has been reflected from the reagent layer and travels toward the photodetector, may be utilized. As such means, besides the means for simply blocking the light, the means, which changes the intensity of the light or the direction of the optical path of the light by the utilization of light interference, refraction, or diffraction, may be employed. Alternatively, instead of the light being blocked optically, electric power supplied to the light source for producing the measuring light may be blocked, and the photo detection signal S obtained from the photodetector at this time may be taken as the photo detection signal obtained in cases where the reflectivity is 0%.

In order to obtain the photo detection signal S in cases where the reflectivity of the reagent layer with respect to the measuring light is 100%, besides the white plate 23W of the dummy unit 10W shown in FIG. 15, operation may be performed, wherein the measuring light is irradiated to a gray plate, a blue plate, a green plate, a yellow plate, and a red plate, whose optical densities are known. From the photo detection signal S obtained at this time, the photo detection signal S at the time of 100% reflectivity may be calculated.

Also, a black plate, which is of the same type as the black plate 23K of the dummy unit 10K described above, and a white plate, which is of the same type as the white plate 23W of the dummy unit 10W, may be formed at certain areas of the reagent layer 24. The measuring light may be irradiated to the black plate and the white plate. In this manner, the photo detection signal S at the time of the 0% reflectivity and the photo detection signal S at the time of the 100% reflectivity may be obtained.

Further, the technique, with which the blood testing apparatus makes a judgment as to the start point of the color forming reaction of the reagent layer, is not limited to the technique for measuring the intensity of the light reflected from the reagent layer. Specifically, a certain region or the entire region of the blood testing unit may be brought into direct or indirect contact with the blood testing apparatus, and the judgment as to the start point of the color forming reaction of the reagent layer may thus be made. As another alternative, a signal representing the start of the color forming reaction may be fed into the blood testing apparatus with a manual operation, which is performed simultaneously with the loading of the blood testing unit into the blood testing apparatus.

Although the embodiments of the present invention are described above for the blood testing apparatus, the present invention is applicable to tests of bodily fluids other than blood, and the similar effects are capable of being obtained.

What is claimed is:

1. A humoral testing apparatus for use with a humoral testing unit, in which measuring light is irradiated to a reagent area of a reagent layer, the reagent area forming a color as a result of a reaction with a humoral sample, and an optical density of the reagent area is detected in accordance with a light intensity of the light reflected from the reagent area, comprising:

a light guide member;

two or more measuring lights having wavelengths different from each other alternatively irradiating the reagent layer through the light guide member;

means for performing a plurality of independent light intensity detecting operations with respect to a plurality of subareas of the reagent area of the reagent layer, each of the independent light intensity detecting operations being performed for one of the plurality of the subareas of the reagent area; and means for statistically processing results of the plurality of the independent light intensity detecting operations performed with respect to the plurality of the subareas of the reagent area, a light intensity value representative of the one of plurality of subareas of the reagent area being obtained from the statistical processing, wherein the means for performing the detecting operations includes a two-dimensional photodetector with a plurality of pixels for performing the plurality of independent light intensity detecting operations with respect to the subareas of the reagent area, and wherein the means for statistically processing is adapted to process a mean value, a median value, a normal distribution, or a mean value of the detected light intensity values, which falls with a range of plus or minus 2 standard deviations (SD) around a detected light intensity value that is associated with a maximum frequency of occurrence, and said two-dimensional photodetector detecting the intensity value of the reflected light.

2. The humoral testing apparatus according to claim 1, wherein said subareas comprise at least one detecting spot and a plurality of data is obtained from the plurality of pixels which detect light reflected from said at least one detecting spot of analyte and the plurality of data is statistically processed.

3. The humoral testing apparatus according to claim 1, wherein the wavelengths of two of the two or more measuring lights are 505 nm and 650 nm respectively.

4. The humoral testing apparatus according to claim 2, wherein the wavelengths of two of the two or more measuring lights are 505 nm and 650 nm respectively.

5. The humoral testing apparatus according to claim 1, wherein the two or more measuring lights alternatively irradiate the reagent layer through the light guide member at periodic intervals.

6. The humoral testing apparatus according to claim 2, wherein the two or more measuring lights alternatively irradiate the reagent layer through the light guide member at periodic intervals.

7. The humoral testing apparatus according to claim 3, wherein the two or more measuring lights alternatively irradiate the reagent layer through the light guide member at periodic intervals.

8. The humoral testing apparatus according to claim 4, wherein the two or more measuring lights alternatively irradiate the reagent layer through the light guide member at periodic intervals.

* * * * *